US012576230B2

(12) United States Patent
Slight et al.

(10) Patent No.: US 12,576,230 B2
(45) Date of Patent: Mar. 17, 2026

(54) PATIENT INTERFACE AND ASPECTS THEREOF

(71) Applicant: FISHER & PAYKEL HEALTHCARE LIMITED, Auckland (NZ)

(72) Inventors: Matthew Robert Geoff Slight, Auckland (NZ); Charles Nicolson, Auckland (NZ); Jeroen Hammer, Auckland (NZ); Wen Dong Huang, Auckland (NZ); Arvin San Jose Gardiola, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 18/405,343

(22) Filed: Jan. 5, 2024

(65) Prior Publication Data

US 2024/0198028 A1     Jun. 20, 2024

Related U.S. Application Data

(63) Continuation of application No. 17/142,647, filed on Jan. 6, 2021, now Pat. No. 11,925,759, which is a continuation of application No. 14/905,480, filed as application No. PCT/NZ2014/000150 on Jul. 17, 2014, now Pat. No. 10,918,818.

(60) Provisional application No. 61/990,328, filed on May 8, 2014, provisional application No. 61/847,452, filed on Jul. 17, 2013.

(51) Int. Cl.
*A61M 16/06* (2006.01)

(52) U.S. Cl.
CPC ........ *A61M 16/0622* (2014.02); *A61M 16/06* (2013.01); *A61M 16/0666* (2013.01); *A61M 16/0683* (2013.01)

(58) Field of Classification Search
CPC .............. A61M 16/0622; A61M 16/06; A61M 16/0666; A61M 16/0683; A61M 2016/0661
See application file for complete search history.

(56) References Cited

U.S. PATENT DOCUMENTS

| | | | |
|---|---|---|---|
| 4,167,185 A | 9/1979 | Lewis | |
| 4,665,570 A | 5/1987 | Davis | |
| 4,739,755 A | 4/1988 | White et al. | |

(Continued)

FOREIGN PATENT DOCUMENTS

| | | |
|---|---|---|
| CN | 1681553 A | 10/2005 |
| CN | 1784250 A | 6/2006 |

(Continued)

OTHER PUBLICATIONS

Written Opinion; PCT/NZ2014/000150; dated Nov. 17, 2014; 4 pages.

(Continued)

Primary Examiner — Elliot S Ruddie
(74) Attorney, Agent, or Firm — VIA LLP

(57) ABSTRACT

A ballooning patient interface has a frame that supports a scaling member. The frame and/or the scaling member is scoured to the head of a user with headgear, such as a strap. Various features of the sealing member improve comfort for the user in the nares of the users as well as on facial surfaces in contact with the seating member.

22 Claims, 24 Drawing Sheets

(56) References Cited

U.S. PATENT DOCUMENTS

| | | | |
|---|---|---|---|
| 4,794,921 | A | 1/1989 | Lindkvist |
| 5,724,965 | A | 3/1998 | Handke et al. |
| 6,431,172 | B1 | 8/2002 | Bordewick |
| 6,834,650 | B1 | 12/2004 | Fini et al. |
| 6,892,730 | B2 | 5/2005 | Griffiths |
| 7,237,551 | B2 | 7/2007 | Ho et al. |
| 7,287,528 | B2 | 10/2007 | Ho et al. |
| 7,308,895 | B2 | 12/2007 | Wixey et al. |
| 7,681,575 | B2 | 3/2010 | Wixey et al. |
| 8,602,029 | B2 | 12/2013 | Gradon et al. |
| 8,869,797 | B2 | 10/2014 | Davidson et al. |
| 8,887,725 | B2 | 11/2014 | Hernandez et al. |
| 9,056,178 | B2 | 6/2015 | McAuley et al. |
| 10,232,135 | B2 | 3/2019 | Siew et al. |
| 10,918,818 | B2 | 2/2021 | Slight et al. |
| 10,953,179 | B2 | 3/2021 | Siew et al. |
| 11,925,759 | B2 | 3/2024 | Slight et al. |
| 2001/0020474 | A1 | 9/2001 | Hecker et al. |
| 2002/0033175 | A1 | 3/2002 | Bateman et al. |
| 2002/0053347 | A1 | 5/2002 | Ziaee |
| 2003/0019495 | A1 | 1/2003 | Palkon et al. |
| 2004/0107968 | A1 | 6/2004 | Griffiths |
| 2004/0216747 | A1 | 11/2004 | Jones, Jr. et al. |
| 2004/0226566 | A1 | 11/2004 | Gunaratnam et al. |
| 2005/0028822 | A1 | 2/2005 | Sleeper |
| 2005/0257792 | A1 | 11/2005 | Wixey et al. |
| 2006/0060200 | A1 | 3/2006 | Ho et al. |
| 2006/0096598 | A1* | 5/2006 | Ho .................... A61M 16/0616 |
| | | | 128/206.24 |
| 2006/0162729 | A1 | 7/2006 | Ging |
| 2006/0237018 | A1 | 10/2006 | McAuley et al. |
| 2007/0089749 | A1 | 4/2007 | Ho et al. |
| 2007/0221227 | A1 | 9/2007 | Ho et al. |
| 2008/0006277 | A1 | 1/2008 | Worboys et al. |
| 2008/0110464 | A1 | 5/2008 | Davidson et al. |
| 2008/0295846 | A1 | 12/2008 | Han et al. |
| 2009/0000623 | A1 | 1/2009 | Lynch et al. |
| 2009/0107504 | A1 | 4/2009 | McAuley |
| 2010/0018534 | A1 | 1/2010 | Veliss et al. |
| 2010/0192957 | A1 | 8/2010 | Hobson et al. |
| 2010/0294281 | A1* | 11/2010 | Ho .................... A61M 16/0633 |
| | | | 128/206.24 |
| 2010/0326441 | A1 | 12/2010 | Zucker |
| 2011/0088699 | A1 | 4/2011 | Skipper et al. |
| 2011/0146685 | A1* | 6/2011 | Allan ................ A61M 16/0816 |
| | | | 128/206.26 |
| 2011/0186051 | A1 | 8/2011 | McAuley et al. |
| 2011/0290253 | A1 | 12/2011 | McAuley et al. |
| 2012/0080035 | A1 | 4/2012 | Guney et al. |
| 2012/0132208 | A1 | 5/2012 | Judson et al. |
| 2013/0019870 | A1 | 1/2013 | Collazo et al. |
| 2013/0152935 | A1 | 6/2013 | Sher |
| 2013/0199537 | A1 | 8/2013 | Formica et al. |
| 2014/0326243 | A1 | 11/2014 | Znamenskly et al. |
| 2014/0326246 | A1 | 11/2014 | Chodkowski et al. |
| 2021/0260323 | A1 | 8/2021 | Siew et al. |

FOREIGN PATENT DOCUMENTS

| | | | | |
|---|---|---|---|---|
| CN | 1993153 | A | 7/2007 | |
| CN | 101541380 | | 9/2009 | |
| CN | 101951984 | A | 1/2011 | |
| CN | 102271744 | | 12/2011 | |
| CN | 102648018 | | 8/2012 | |
| CN | 102892450 | A | 1/2013 | |
| CN | 203017605 | | 6/2013 | |
| DE | 102006016125 | A1 | 10/2007 | |
| EP | 2140902 | A1 | 1/2010 | |
| EP | 2145645 | | 1/2010 | |
| JP | 2001299915 | A | 10/2001 | |
| JP | 2007-516750 | | 6/2007 | |
| JP | 2007527271 | | 9/2007 | |
| JP | 2008-525123 | A | 7/2008 | |
| JP | 2009-504320 | | 2/2009 | |
| JP | 2009-517185 | | 4/2009 | |
| JP | 2012-526592 | | 11/2012 | |
| JP | 2016527973 | | 9/2016 | |
| NZ | 570059 | | 8/2010 | |
| TW | 201306887 | | 2/2013 | |
| WO | WO 2001/062326 | | 8/2001 | |
| WO | WO 2001/097892 | | 12/2001 | |
| WO | WO 2004/007010 | | 1/2004 | |
| WO | WO 2004/071565 | | 8/2004 | |
| WO | WO 2005/118040 | | 12/2005 | |
| WO | WO 2006/074513 | | 7/2006 | |
| WO | WO 2007/064660 | | 6/2007 | |
| WO | WO 2008/148086 | | 12/2008 | |
| WO | WO 2010/131189 | | 11/2010 | |
| WO | WO-2010131189 | A1 * | 11/2010 | ............ A61M 16/06 |
| WO | WO 2010/139014 | | 12/2010 | |
| WO | WO 2011/014931 | | 2/2011 | |
| WO | WO-2011014931 | A1 * | 2/2011 | ............ A61M 16/06 |
| WO | WO 2012/020359 | | 2/2012 | |
| WO | WO 2012/047121 | | 4/2012 | |
| WO | WO 2013/041996 | | 3/2013 | |
| WO | WO 2013/066195 | | 5/2013 | |
| WO | WO 2014/021722 | | 2/2014 | |
| WO | WO 2015/009172 | | 1/2015 | |

OTHER PUBLICATIONS

International Search Report; PCT/NZ2014/000150; dated Nov. 17, 2014; 4 pages.

* cited by examiner

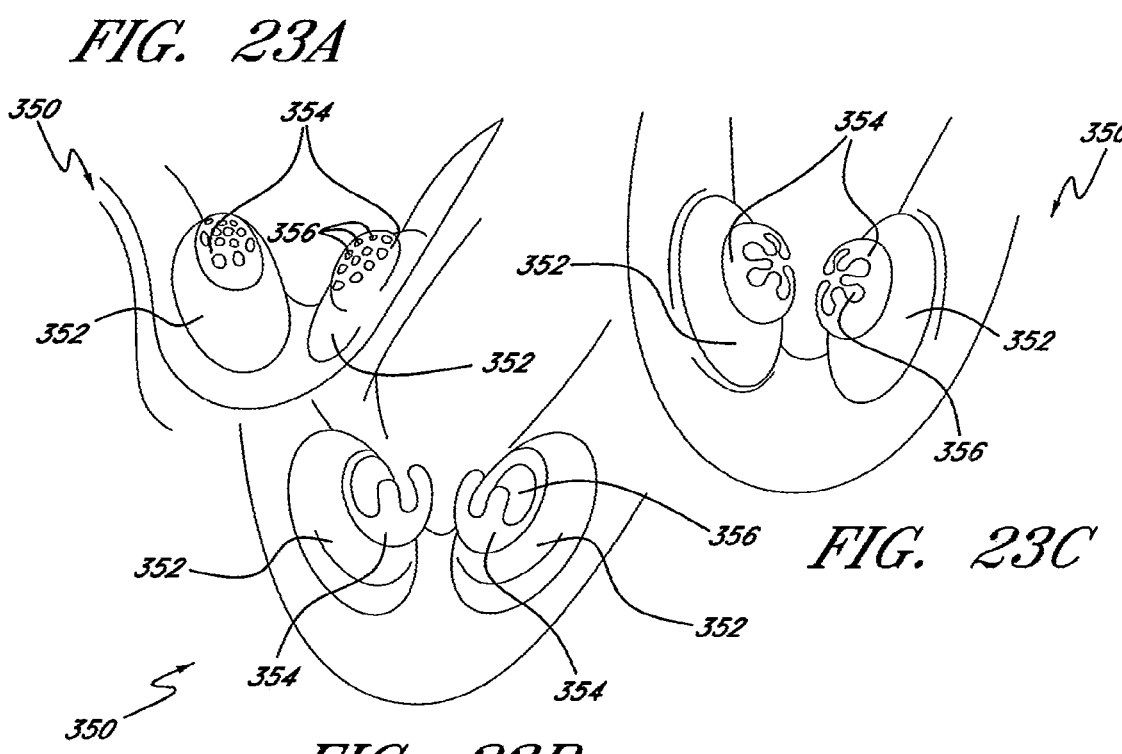
*FIG. 23A*
*FIG. 23C*
*FIG. 23B*
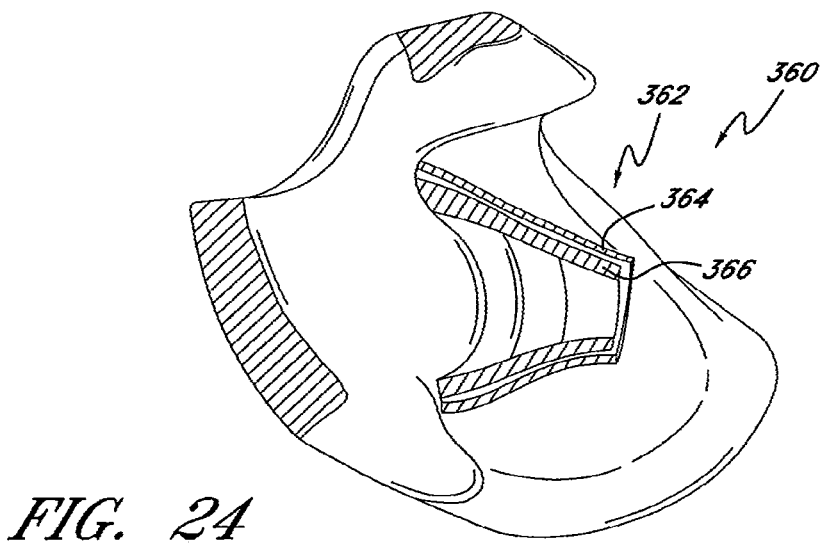
*FIG. 24*

PATIENT INTERFACE AND ASPECTS THEREOF

INCORPORATION BY REFERENCE TO ANY PRIORITY APPLICATIONS

The present application is a continuation application of U.S. patent application Ser. No. 17/142,647, filed on Jan. 6, 2021, which is a continuation application of U.S. patent application Ser. No. 14/905,480, filed on Jan. 15, 2016, now U.S. Pat. No. 10,918,818, issued on Feb. 16, 2021, which is a 371 of International PCT/NZ2014/000150, filed on Jul. 17, 2014, which claims priority benefit of U.S. Provisional Application Ser. No. 61/990,328, filed on May 8, 2014, and claims priority benefit of U.S. Provisional Application Ser. No. 61/847,452, filed on Jul. 17, 2013, the disclosures of each of which are hereby incorporated by reference in its entirety. Any and all applications for which a foreign or domestic priority claim is identified in the Application Data Sheet as filed with the present application are hereby incorporated by reference herein in their entireties and made a part of the present disclosure.

BACKGROUND OF THE INVENTION

Field of the Invention

The present invention generally relates to interfaces for providing a supply of pressurised gas to a recipient.

Description of the Related Art

Breathing gases can be delivered to users with a variety of different mask styles and can be delivered for a variety of different purposes. For example, users can be ventilated using non-invasive ventilation (NIV). In addition, continuous positive airway pressure (CPAP) or variable airway pressure can be delivered using masks to treat a medical disorder, such as obstructive sleep apnea (OSA), chronic obstructive pulmonary disease (COPD), or congestive heart failure (CHF).

These non-invasive ventilation and pressure support therapies generally involve the placement of a user interface device, which is typically a nasal or nasal/oral mask, on the face of a user. The flow of breathing gas can be delivered from the pressure/flow generating device to the airway of the user through the mask.

Typically, patient interface devices include a mask frame that supports a sealing member. The sealing member contacts the facial surfaces of the user, including regions surrounding the nose, including the nose and the nares. Because such masks are typically worn for an extended period of time, a variety of concerns must be taken into consideration. For example, in providing CPAP to treat OSA, the user normally wears the mask all night long while he or she sleeps. One concern in such a situation is that the mask should be as comfortable as possible. It is also important that the mask provide a sufficient seal against a user's face without significant discomfort.

SUMMARY OF THE INVENTION

Accordingly, it is an object of certain embodiments of the present invention to provide an improved sealing member for use in a mask assembly that overcomes the shortcomings of conventional sealing members.

In some configurations, a nasal seal configured to be removably coupled to a frame of a patient interface or a patient interface incorporating a seal includes a seal body formed of a soft flexible material and defining an inner cavity and one or more delivery openings for supply of breathing gases from the inner cavity to the patient. The seal body comprises a central portion and a side portion extending from each end of the central portion. The seal body further comprises an interior side and an exterior side, wherein the interior side of the central portion is configured to extend across a base of a user's nose and the interior side of each of the side portions is configured to extend across a side of the nose. The interior side of the seal is supple and configured to conform under internal pressure to surfaces of the user's nose, including, at the side portions of the seal, to outside surfaces of the side of the nose. Each of the side portions defines a transition portion between the exterior side and the interior side, wherein the exterior side of each of the side portions comprises stiffened regions that are stiffer or much stiffer than the supple interior side, the stiffened regions extending to or substantially to the transition portions.

In some such configurations, the stiffened regions are formed by relatively thickened portions of the seal body. The thickened portions can taper in thickness before the transition portions. The transition portions can include a portion that is thicker than the supple interior side.

In some such configurations, the stiffened regions extend substantially along an entire length of the exterior side of the seal body.

In some such configurations, the transition portions comprise rounded wall sections.

In some such configurations, a support is formed of a relatively rigid material and supports a portion of the seal body. The support can define at least one grip surface portion extending along the exterior side of the seal body. The at least one grip surface portion can comprise at least one pair of grip surface portions substantially opposite one another.

In some such configurations, the support defines a mount for mounting the nasal seal to the frame. The mount can comprise a first member that is connectable to a second member, wherein the first member and the second member capture a portion of the seal body between them. The first member can be positioned within a cavity of the seal body and can comprise a sleeve portion that extends outwardly from the cavity. The second member can surround the sleeve portion of the first member.

In some such configurations, the stiffened regions are disposed in rearmost and lowermost sections of the side portions. The rearmost and lowermost sections of the side portions can flare outwardly relative to adjacent portions of the seal body.

In some such configurations, the one or more delivery openings comprise a first delivery opening and a second delivery opening. The nasal seal can further comprise a nostril locator associated with and forming a portion of each delivery opening, wherein a deflection region is defined within an annular transition portion between each of the nostril locators and a surrounding portion of the interior side. The deflection region has a lower stiffness relative to another region of the annular transition portion not within the deflection region.

In some such configurations, the lower stiffness is achieved by the deflection regions having a smaller thickness than the other regions of the annular transition portion. The deflection regions can be located on the outer sides of the nostril locators. The deflection regions can be limited to less than or equal to one-half of the annular transition portion.

In some such configurations, the central portion of the seal body defines a thinned region that permits forward movement of an upper portion of the interior side of the central portion as a result of rolling movement of the seal body.

In some configurations, a nasal seal configured to be removably coupled to a frame of a patient interface or a patient interface incorporating a seal includes a seal body formed of a soft flexible material and defining an inner cavity and one or more delivery openings for supply of breathing gases from the inner cavity to the patient. The seal body comprises a central portion and a side portion extending from each end of the central portion. The seal body further comprises an interior side and an exterior side, wherein the interior side of the central portion is configured to extend across a base of a user's nose and the interior side of each of the side portions is configured to extend across a side of the nose. The interior side of the seal is supple and configured to conform under internal pressure to surfaces of the user's nose, including, at the side portions of the seal, to outside surfaces of the side of the nose. The exterior side of each of the side portions comprises stiffened regions that are stiffer or much stiffer than the supple interior side, the stiffened regions being disposed in a rearmost and lowermost sections of the side portions.

In some such configurations, the rearmost and lowermost sections of the side portions flare outwardly relative to adjacent portions of the seal body.

In some such configurations, the flared side portions are generally aligned with surfaces of the user's cheek or upper lip laterally outward of the nose.

In some such configurations, the stiffened regions are formed by relatively thickened portions of the seal body.

In some such configurations, the thickened portions taper in thickness before transition portions between the interior side and the exterior side.

In some such configurations, the transition portions include a portion that is thicker than the supple interior side.

In some configurations, a nasal seal configured to be removably coupled to a frame of a patient interface or a patient interface incorporating a seal includes a seal body formed of a soft flexible material and defining an inner cavity and one or more delivery openings for supply of breathing gases from the inner cavity to the patient. The seal body comprises a central portion and a side portion extending from each end of the central portion. The seal body further comprises an interior side and an exterior side. The interior side of the central portion is configured to extend across a base of a user's nose and the interior side of each of the side portions is configured to extend across a side of the nose. The interior side of the seal is supple and configured to conform under internal pressure to surfaces of the user's nose, including, at the side portions of the seal, to outside surfaces of the side of the nose. The exterior side of each of the side portions comprises stiffened regions that are stiffer or much stiffer than the supple interior side. The exterior side of the seal body further defines a grip surface on each of the side portions, the grip surfaces located on the stiffened regions.

In some such configurations, the grip surface is formed by a protrusion.

In some such configurations, the protrusion is generally crescent-shaped, thereby defining a generally scallop-shaped grip surface.

In some such configurations, the ends of the protrusion are positioned rearward of the center, curved portion of the protrusion.

In some configurations, a nasal seal configured to be removably coupled to a frame of a patient interface or a patient interface incorporating a seal includes a seal body formed of a soft flexible material and defining an inner cavity and one or more delivery openings for supply of breathing gases from the inner cavity to the patient. The seal body comprises a central portion and a side portion extending from each end of the central portion. The seal body further comprises an interior side and an exterior side. The interior side of the central portion is configured to extend across a base of a user's nose and the interior side of each of the side portions is configured to extend across a side of the nose. The interior side of the seal is supple and configured to conform under internal pressure to surfaces of the user's nose, including, at the side portions of the seal, to outside surfaces of the side of the nose. The nasal seal further comprises a support formed of a relatively rigid material and supporting a portion of the seal body. The support defines at least one grip surface portion extending along the exterior side of the seal body.

In some such configurations, the support defines at least one grip surface portion extending along the exterior side of the seal body.

In some such configurations, the at least one grip surface portion comprises at least one pair of grip surface portions substantially opposite one another.

In some such configurations, the support defines a mount for mounting the nasal seal to the frame.

In some such configurations, the mount comprises a first member that is connectable to a second member, wherein the first member and the second member capture a portion of the seal body between them.

In some such configurations, the first member is positioned within a cavity of the seal body and comprises a sleeve portion that extends outwardly from the cavity.

In some such configurations, the second member surrounds the sleeve portion of the first member.

In some configurations, a nasal seal configured to be removably coupled to a frame of a patient interface or a patient interface incorporating a seal includes a seal body formed of a soft flexible material and defining an inner cavity. The seal body comprises a central portion and a side portion extending from each end of the central portion. The seal body further comprises an interior side and an exterior side. The interior side of the central portion is configured to extend across a base of a user's nose and the interior side of each of the side portions is configured to extend across a side of the nose. The interior side of the seal is supple and configured to conform under internal pressure to surfaces of the user's nose, including, at the side portions of the seal, to outside surfaces of the side of the nose. The seal body comprises a first delivery opening and a second delivery opening for supply of breathing gases from the inner cavity to the nostrils of the user. A nostril locator is associated with and forms a portion of each delivery opening. A deflection region is defined within a transition portion between each of the nostril locators and a surrounding portion of the interior side. The deflection region has a lower stiffness relative to another region of the transition portion not within the deflection region.

In some configurations, the deflection regions have a lower thickness than the other region of the transition portion.

In some configurations, the deflection regions are located on an outer side of the nostril locators to facilitate movement of the nostril locators outwardly away from one another.

In some configurations, the deflection regions are limited to less than or equal to one-half of the transition portion, which can be generally annular in shape.

In some configurations, a patient interface or a seal arrangement for a patient interface comprises a first delivery opening and a second delivery opening for supply of breathing gases from the inner cavity to the nostrils of the user. A nostril locator or seal member (e.g., nasal pillow) is associated with and forms a portion of each delivery opening. A deflection region is defined within an annular transition portion between each of the nostril locators or seal members and a surrounding portion of the seal arrangement. The deflection region has a lower stiffness relative to another region of the transition portion not within the deflection region. The lower stiffness may be accomplished by a lower wall thickness within the deflection region compared to the other region. The deflection region may be located on the outsides of the nostril locators or seal members to facilitate outward tilting. The deflection region may be limited to less than or equal to about one-half of the annular transition portion, which can be generally annular in shape.

In some configurations, a sealing member is provided for a mask with the sealing member having any set or subset of features or any combination of sets or subsets of features described herein. In some such configurations, a mask can have such a sealing member.

In some configurations, a seal member comprises a proximal surface and a distal surface. The proximal surface has one or more delivery openings for supply of breathing gases to the patient. The proximal surface and the distal surface define an inner cavity within the seal member. At least one integrated support structure underlies at least a portion of the inner cavity.

In some such configurations, the at least one integrated support structure comprises a crescent shaped member that is structurally integrated into the seal member.

In some such configurations, the at least one integrated support structure extends at least partially upward along at least a portion of the distal surface. In some such configurations, the at least one integrated support structure extends upwardly along the distal surface. In some such configurations, a portion of the at least one integrated support structure that extends upwardly along the distal surface extends proximally and is configured to provide support relative to a region of a user along a cheek region.

In some such configurations, the portion of the integrated support structure that underlies the inner cavity extends proximally and is configured to provide support relative to a region of a user just above a lip.

In some such configurations, the integrated support structure comprises one or more thickened regions of the seal member. In some such configurations, the thickened regions incorporate a hollow region having another material positioned within hollow region of the integrated support structure.

In some such configurations, the at least one integrated support structure is positioned in a marginal surface that connects the proximal surface to the distal surface. In some such configurations, the marginal surface is wider at a bottom portion than at a top portion. In some such configurations, the seal member has a thicker wall in a region that includes the bottom portion of the marginal surface relative to a region generally surrounding the one or more delivery openings. In some such configurations, the region with the thicker wall extends upwardly from the bottom portion of the marginal surface.

In some such configurations, the at least one integrated support structure is positioned to be in a widest lateral region of the seal member.

In some such configurations, the at least one integrated support structure extends most proximally of any other portion of the seal member.

In some such configurations, the at least one integrated support structure is positioned to be in a widest lateral region of the seal member and extends most proximally of any other portion of the seal member.

Various features, aspects and advantages of the present invention can be implemented in any of a variety of manners. For example, while several embodiments will be described herein, sets or subsets of features from any of the embodiments can be used with sets or subsets of features from any of the other embodiments.

The term "comprising" is used in the specification and claims, means "consisting at least in part of". When interpreting a statement in this specification and claims that includes "comprising", features other than that or those prefaced by the term may also be present. Related terms such as "comprise" and "comprises" are to be interpreted in the same manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

BRIEF DESCRIPTION OF THE DRAWINGS

These and other features, aspects and advantages of the present invention will be described with reference to the following drawings.

FIGS. 23A-23C are views of portions of interface assemblies that are arranged and configured in accordance with certain features, aspects and advantages of the present invention.

FIG. 24 is a view of a portion of an interface assembly that is arranged and configured in accordance with certain features, aspects and advantages of the present invention.

DETAILED DESCRIPTION OF THE PREFERRED EMBODIMENTS

Figure 1:
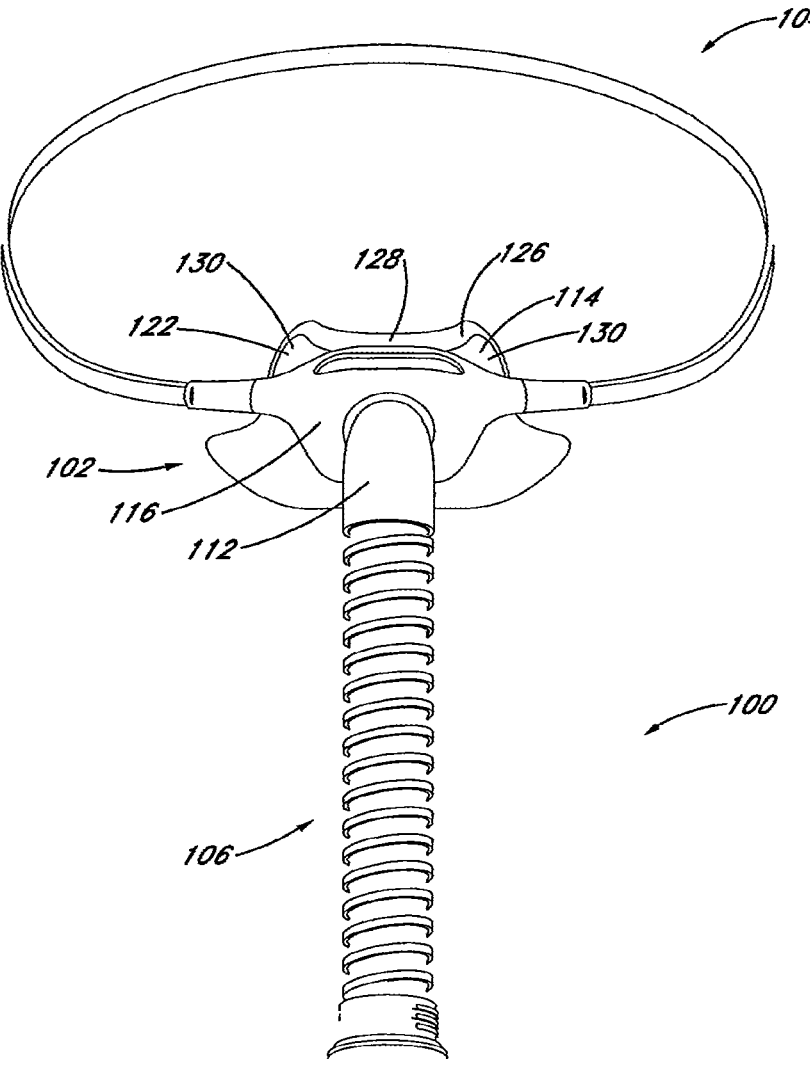
FIG. 1 is a front view of an interface assembly that is arranged and configured in accordance with certain features, aspects and advantages of the present invention.

FIG. 1 illustrates a patient interface 100 that is arranged and configured in accordance with certain features, aspects and advantages of the present invention. The interface 100 can be used to supply pressurized breathing gases to a recipient. The interface 100 is well suited for providing breathing gases to the recipient in situations where significant pressure changes are likely to be encountered. For example but without limitation, the interface 100 can be used for delivering continuous positive airway pressure (CPAP).

With continued reference to FIG. 1, the interface 100 is shown separate from a patient who would wear the interface 100. Some aspects of the patient interface 100, and variations on each aspect, have been described in U.S. patent application Ser. No. 12/945,141, filed Nov. 12, 2010, which is hereby incorporated by reference in its entirety. The interface 100 broadly comprises a mask 102. In some configurations, a strap 104 can attach to the mask 102 and can be used to secure the mask 102 to the patient. In some configurations, the interface 100 also comprises a flexible supply conduit 106 that can connect to the mask 102.

Figure 2:
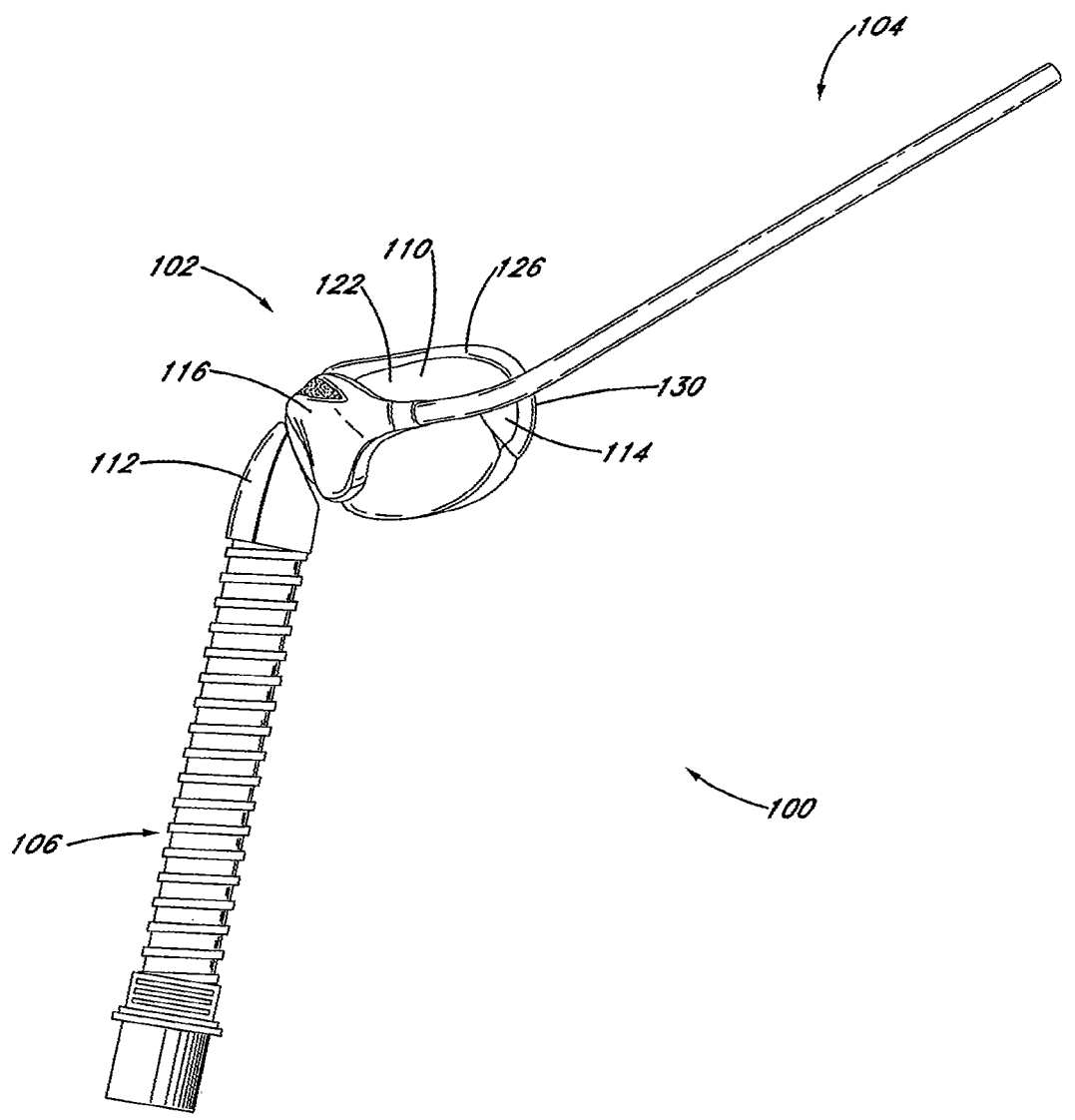
FIG. 2 is a side view of the interface assembly of FIG. 1.

With continued reference to FIG. 1 and with additional reference to FIG. 2, the mask 102 is configured to fit over or overlie both nostrils of the patient. In some configurations, the mask 102 can include lateral portions 110 (see FIG. 2) that are configured to curve around toward each lateral side of a nose of the patient. These lateral portions 110 can form a perimeter seal on outwardly facing surfaces of flanks of the nose. The strap 104 can pass around the user's head in a simple loop above the user's ears.

The flexible conduit 106 can depend from a central connection 112. In some configurations, the central connection 112 can be positioned at a frontal portion of the mask 102. The central connection 112 preferably comprises a swiveling elbow. The elbow can enable the flexible conduit 106 to pivot relative to the mask 102. By enabling pivoting, the elbow can help the interface 100 to better adapt to the sleeping position of the patient. In some configurations, the central connection 112 may comprise a ball joint so that the elbow can pivot about axes parallel to and perpendicular to its connection with the mask 102.

The illustrated mask 102 generally comprises a seal 114 and a body or frame 116. The seal 114 and the frame 116 can be connected in any suitable manner.

The seal 114 preferably defines a supple pocket or envelope that can contain a recess region. In some configurations, the seal 114 can comprise a low wall thickness and can be formed of any suitable material. For example but without limitation, the seal 114 can be formed of latex, vinyl, silicone or polyurethane. In some configurations, the wall thickness can be below about 0.5 mm and could be lower than about 0.2 mm in some regions and in some configurations. In some configurations, the seal 114 can be formed of a material having sufficient elasticity and yield strength so that the combination renders the seal 114 supple. The seal 114 preferably is capable of withstanding repeated drastic deformations without failure.

Figure 3:
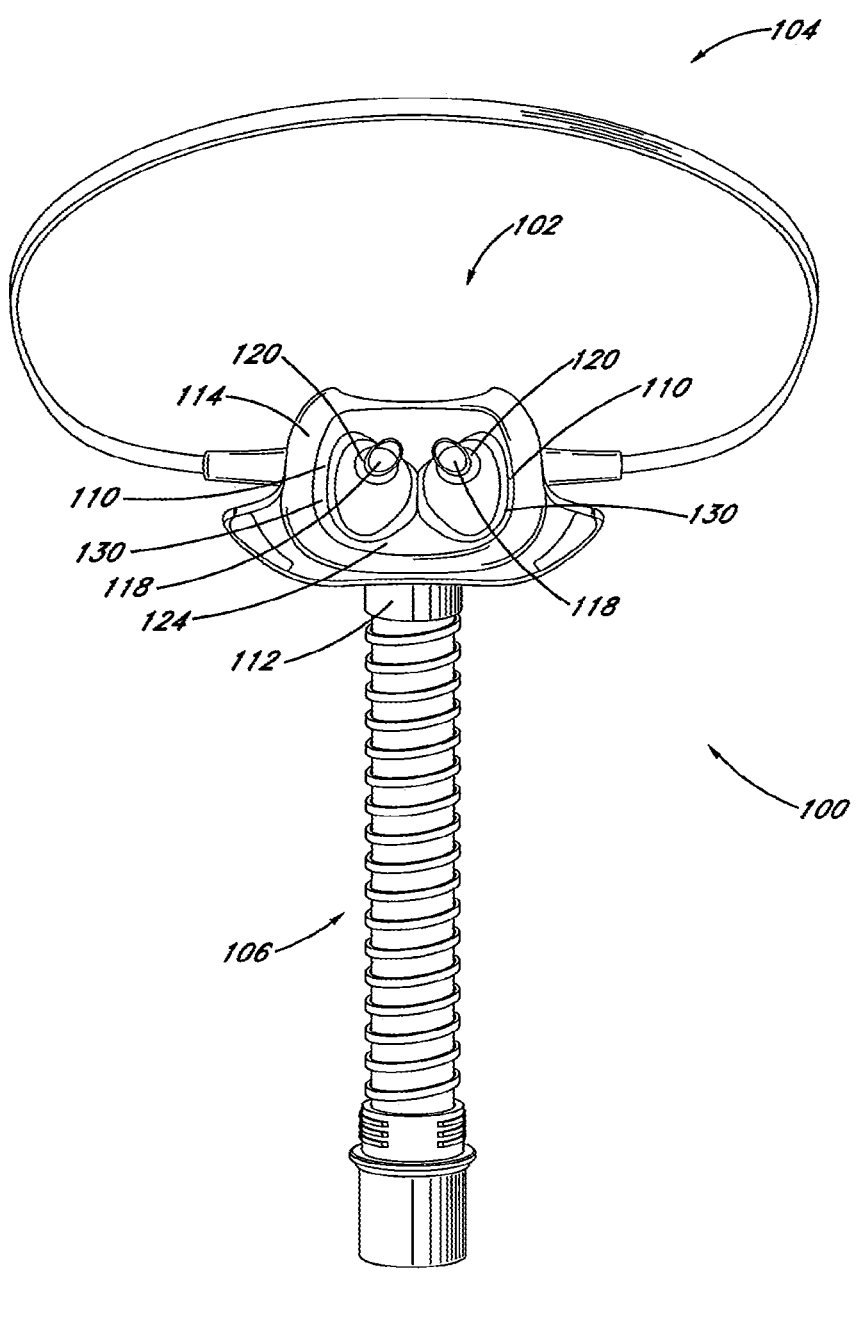
FIG. 3 is a rear view of the interface assembly of FIG. 1.

With reference to FIG. 3, the seal 114 preferably comprises one or two nostril locators 120. The nostril locators 120 can protrude from the seal 114. In some configurations, the nostril locators extend generally upwardly and rearwardly from a proximal wall 124 of the seal 114. In some configurations, the nostril locators 120 extend generally rearwardly from the proximal wall 124 of the seal 114.

In the configuration illustrated in FIGS. 1-3, the nostril locators 120 are formed integrally (i.e., in one monolithic piece) with the seal 114. Each nostril locator 120 can comprise an outlet aperture 118 through which gas can be supplied from the flexible conduit 106. In some configurations, the gas can be supplied from within the pocket or envelope defined by the seal 114. In other configurations, the gas that is supplied can be separate from the gas supplied to the pocket or envelope defined by the seal 114.

The seal 114 generally comprises a distal wall 122 and the proximal wall 124. An outer surface of the distal wall 122 preferably faces away from the user while an outer surface of the proximal wall 124 preferably faces the user. A rim 126 (see FIGS. 1 and 2) can connect an outer perimeter of the distal wall 122 and an outer perimeter of the proximal wall 124. The envelope or pocket described above can be defined within at least the distal wall 122 and the proximal wall 124.

The seal 114 preferably is designed to wrap around the tip or lower portion (e.g., locations below the bridge) of the user's nose. As such, the illustrated seal 114 comprises a central portion 128 (see FIG. 1) positioned between side portions or wings 130. The central portion 128 can underlie the user's nose and preferably incorporates the nostril locators 120. In some configurations, the central portion 128 can extend upward over a tip of the user's nose. In other configurations, the central portion 128 does not extend upward over the tip of the user's nose. The wings 130 can form at least a portion of the lateral portions 110 discussed above. The wings 130 can be configured to extend completely or substantially completely over the sides of the user's nose and may extend at least partially over the user's cheeks.

As described above, at least a substantial portion of the seal 114 can be supple. For example, a region surrounding the nostril locators 120 can be more supple than at least a portion of the wings 130. At least the proximal wall 124 and the rim 126 of each side portion can be very supple so that they can expand to conform to the contours of the user's face, and in particular, to the contours of the outside flanks of the user's nose. Preferably, the supple portions of the seal 114 are of sufficient dimension and shape that, when the inflated seal is pressed against the face of the user with the nostril locators 120 engaged in the nostrils of the user, the seal 114 conforms to the surfaces of the user's face (i.e., at least the sides of the nose and along at least a portion of the upper lip).

Select portions of the seal 114, however, can have an increased rigidity to improve the form, fit and function of the mask 102. For example, at least a portion of the rim 126 can be significantly stiffer to provide control to ballooning of other regions of the seal 114. In addition, a region adjacent to and including an inlet opening (e.g., the portion that receives the flow of gases from the conduit 106) of the seal 114 can be less supple. Thus, the distal wall 122 can have a decreasing suppleness from the wings 130 to the central portion that contains the inlet opening. The less supple regions can be formed of a different material or can be formed of the same material but with an increased thickness.

As described above, the frame 116 supports the seal 114. In some configurations, an inlet opening of the seal 114 can be fitted to the frame 116 and the flexible conduit 106 also can be fitted to the frame 116 such that gases can be provided to the seal 114 through the frame 116. In other configurations, the seal 114 directly connects to the flexible conduit 106. In some configurations, the seal 114 can be connected to the conduit 106 with the central connection 112.

The frame 116 may have any suitable arrangement for securing the seal 114. In some configurations, an annular wall can extend from a proximal side of the frame 116 around a perimeter of an opening that extends to the connector 112. The annular wall can include an outwardly extending lip. The inlet opening of the seal 114 can engage over the outwardly extending lip of the annular wall. In some configurations, the inlet opening of the seal 114 can be stretched to fit over the annular wall. The inlet opening of the seal 114 may be provided with a thickened or reinforced wall section, for example but without limitation. In some configurations, an extended portion of the seal 114 can be rolled up over the annular wall of the frame 116. In another configuration, the seal 114 can be provided with a portion of a connector and at least one of the frame 116 and the conduit 106 may include a complementary connector portion.

The frame 116 can be designed to be minimal in size. Advantageously, the small size of the frame 116 enables a clear field of vision for the user and allows the user to wear glasses while wearing the interface 100. Preferably, the frame 116 is formed from an elastomeric material, which will allow the frame 116 to flex to conform slightly to the face of the user. The frame 116, however, provides support for the seal 114. By providing support for the seal 114, the seal can be more effectively pressed into contact with the face and around the nose of the user. The frame 116 can be formed by injection molding, preferably from an elastomeric material, such as silicone or polyurethane, for example but without limitation. In some configurations, the frame 116 can be formed of more rigid materials, such as polycarbonate, polyester polystyrene, or nylon, for example but without limitation.

In use, the portions of the supple proximal wall 124 that are above, below and to each side of the nostril locators 120 can be inflated by pressure inside the seal 114 (e.g., inflated from the flow of gases supplied to the patient interface 100) to press against the skin of the user and conform to contours of the outside surfaces of the nose of the user, to surfaces of the lower portion of the nose of the user and to surfaces of the upper lip of the user immediately below the nose. Movement of the mask 102 is not likely to significantly break this seal with the face because the supple perimeter or periphery of the seal 114 allows the mask 102 to move in all directions (other than directly away from the face) to at least a small extent. The supple portions of the seal 114 somewhat decouple the position of the nostril locators 120 from the position of the mask 102, which decoupling allows the mask 102 to displace somewhat in at least one or both of the lateral and vertical directions (i.e., lateral and vertical relative to axes of the patient's face). The wings 130 engage the sides of the user's nose and form an additional seal. The wings 130 also support the location of the mask.

Figure 4:
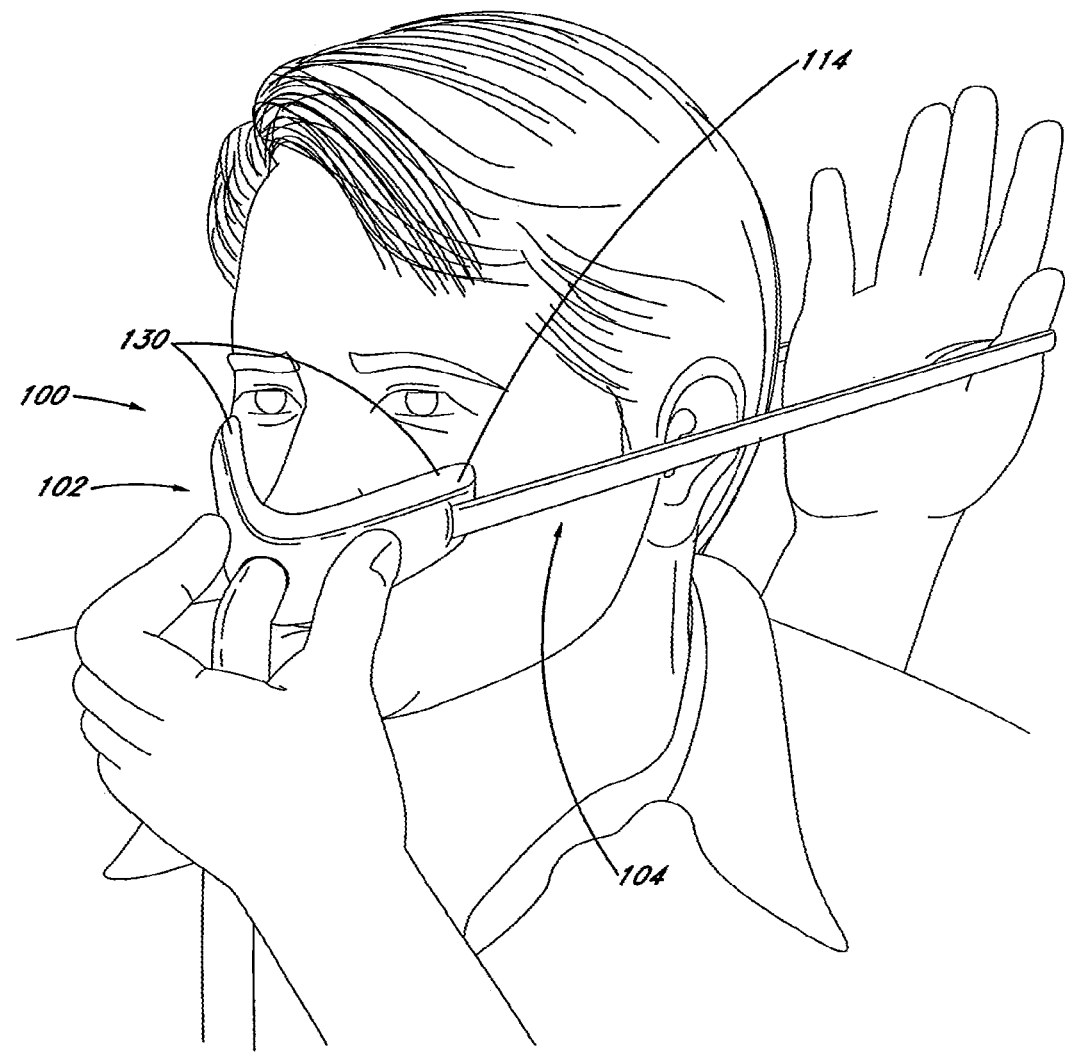
FIG. 4 is an illustration of a user donning an interface assembly having certain characteristics in common with the interface assembly of FIG. 1.

With reference to FIG. 4, when donning the interface 100, the mask 102 can be opened by spreading the wings 130 apart, which increases the angle between the wings 130. With the wings 130 having been pulled open, the nostril locators 120 (see FIG. 3) that are positioned on the proximal wall 124 better present toward the user and guide the location of the mask 102 onto the face of the user. With the nostril locators 120 properly positioned, the mask 102 can be secured in position with the strap 104, which forms a loop around the head of the user at a location vertically higher than the ears. Other techniques for donning the interface also can be used.

As described above, when donning the interface 100, the seal 114 preferably is folded or spread open in order to improve fit and to help achieve a desired positioning. In the configuration of FIGS. 1-4, however, spreading open the seal 114 generally requires that fingers be positioned between the seal 114 and the face of the user, which can be awkward for users. In addition, it can be difficult to open the seal 114 with a single hand such that the other hand can be used to bring the strap 104 into position.

Figure 5:
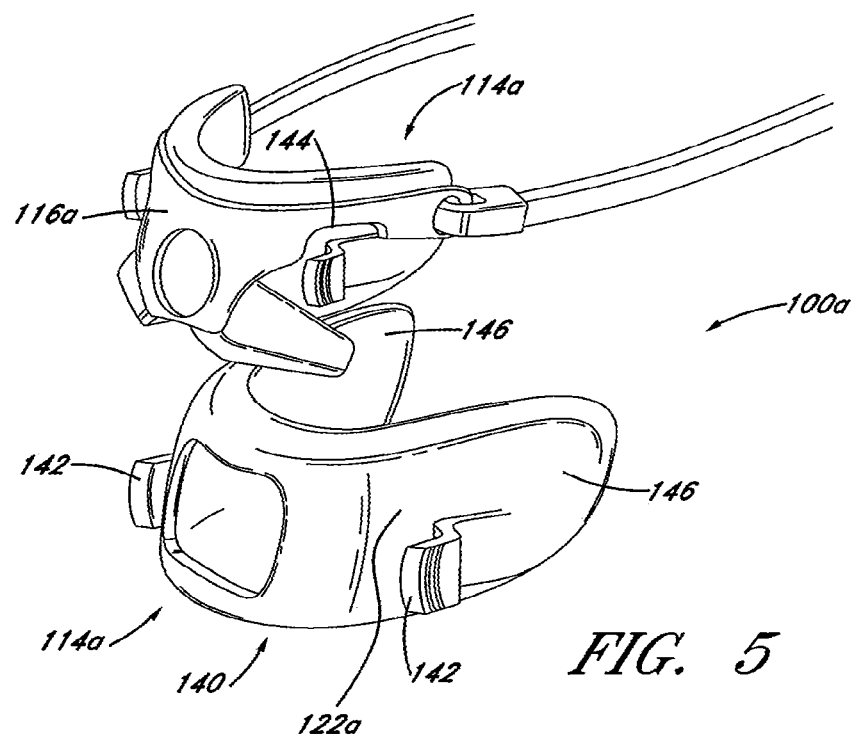
FIG. 5 is a partially exploded view of a portion of an interface assembly that is arranged and configured in accordance with certain features, aspects and advantages of the present invention.

With reference to FIG. 5, an interface 100a is shown with a seal manipulation assembly 140. For clarity, a seal 114a of the interface 100a is shown enlarged and without a frame 116a in the lower portion of FIG. 5 and connected to the frame 116a in the upper portion of FIG. 5. The seal manipulation assembly 140 preferably comprises a pair of pads 142. The pads 142 extend outward from the seal 114a. In some configurations, the pads 142 are positioned along the distal surface 122a. In some configurations, the pads 142 extend outward from the distal surface 122a. In some configurations, the pads 142 are integrally formed with the seal 114a. In some configurations, the pads 142 are separate components from the seal 114a. In the illustrated configuration, a frame 116a of the interface 100a comprises recesses 144 that receive at least a portion of the pads 142. The seal 114a underlies the frame 116a in the region of the pads 142. In some configurations, the seal 114a is not secured to the frame 116a in the region of the pads 142 or proximal of that region such that the seal 114a can be moved relative to the frame 116a.

The pads 142 are connected to an operating mechanism of the seal manipulation assembly 140. In some configurations, the pads 142 are connected to scissor arms that extend within the seal 114a. The scissor arms can cross and be connected with a hinge such that squeezing of the pads 142 toward each other can result in the ends 146 of the seal 114a moving apart from each other.

Figure 6:
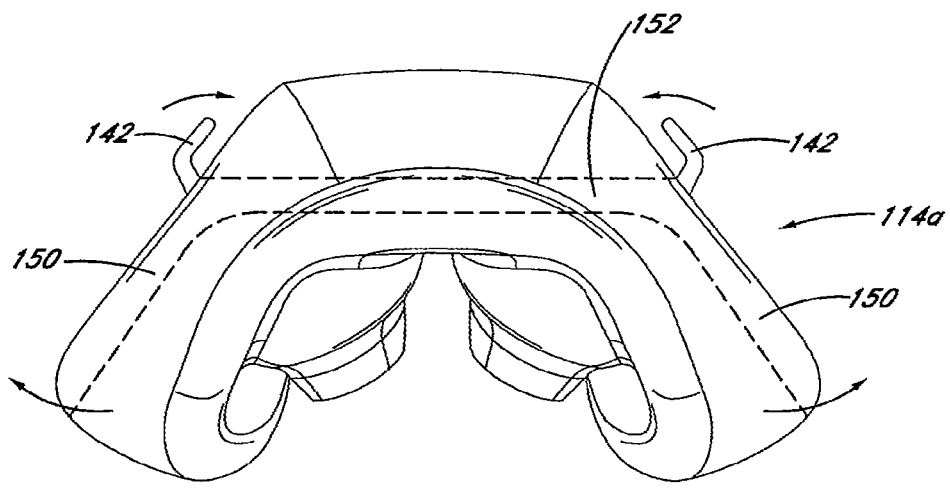
FIG. 6 is a view of a portion of an interface assembly that is arranged and configured in accordance with certain features, aspects and advantages of the present invention.

In some configurations, the operating mechanism is simpler than the scissor mechanism described directly above. For example, with reference to FIG. 6, which is a simplified representation of an operating mechanism, the pads 142 connect to, or are integrally formed with, arms 150. The arms can extend toward the ends 146 of the seal 114a. The arms 150 can have a length that is longer than the length of the pads 142. A forward portion of the arms 150 can be held apart from each other using a cross member 152. In some configurations, the material of the seal 114a, the frame 116a or the seal 114a and the frame 116a combined may be stiff enough to allow separation or spreading of the ends 146 of the seal 114a through manipulation of the pads 142 without including the cross member 152. By holding the arms 150 apart at a location between the pads 142 and the ends 146, depressing the pads 142 toward each other will result in the ends 146 moving apart from each other. In some configurations, the arms 150 can be joined together by a living hinge, by a rigid connection to a flexible cross member that elastically deforms or by a pin joint or the like.

By manipulating the shape of the uninflated seal 114a (e.g., by separating the ends 146a to alter how the seal 114a initially presents itself to the user), the seal 114a is opened for placement onto the face of the user. Once in place, the seal 114a can be inflated, which causes the seal 114a to swell around the nares of the user.

Figure 7:
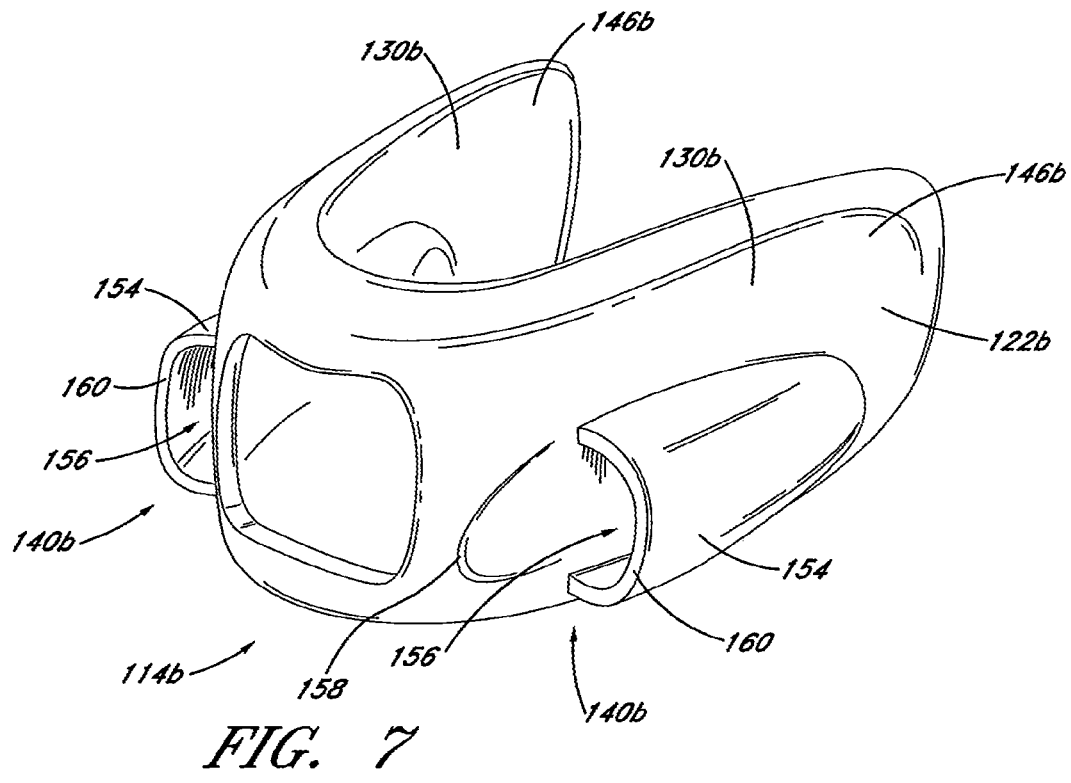
FIG. 7 is a view of a portion of an interface assembly that is arranged and configured in accordance with certain features, aspects and advantages of the present invention.

With reference now to FIG. 7, another seal 114b is illustrated. The seal 114b has been provided with another seal manipulation configuration 140b. In the illustrated seal 114b, the seal manipulation configuration 140b can be attached to or integrally formed with a portion of the distal wall 122b. Preferably, the seal manipulation configuration 140b is positioned along the distal wall 122b along the lateral portions 110b or wings 130b.

The seal manipulation configuration 140b can take any suitable configuration. In some configurations, for example but without limitation, the seal manipulation configuration 140b comprises walls 154 that can define loops of material into which fingers can be inserted. In the illustrated configuration, the seal manipulation configuration 140b comprises pockets 156. Each of the pockets 156 can have a rim 160 at the distal end. The rim 160 can define an opening sufficiently large to receive a finger tip. The proximal end of each of the pockets 156 can be enclosed or open. In the illustrated configuration, the proximal end of each of the pockets 156 is enclosed.

In some configurations, a surface feature 158 can be provided adjacent to the opening defined by the rim 160. The surface feature 158 can be a recess or a surface texture. The surface feature 158 can be positioned just forward of the opening to guide fingers into a desired location. The surface feature 158 can provide additional clearance to facilitate insertion of the fingers.

By positioning the pockets 156 on the outside of the seal 114b, fingers can be inserted into the pockets 156 and the pockets 156 can be used to provide an outward force on the wings 130b to open the seal 114b for presentation to the face.

Figure 8:
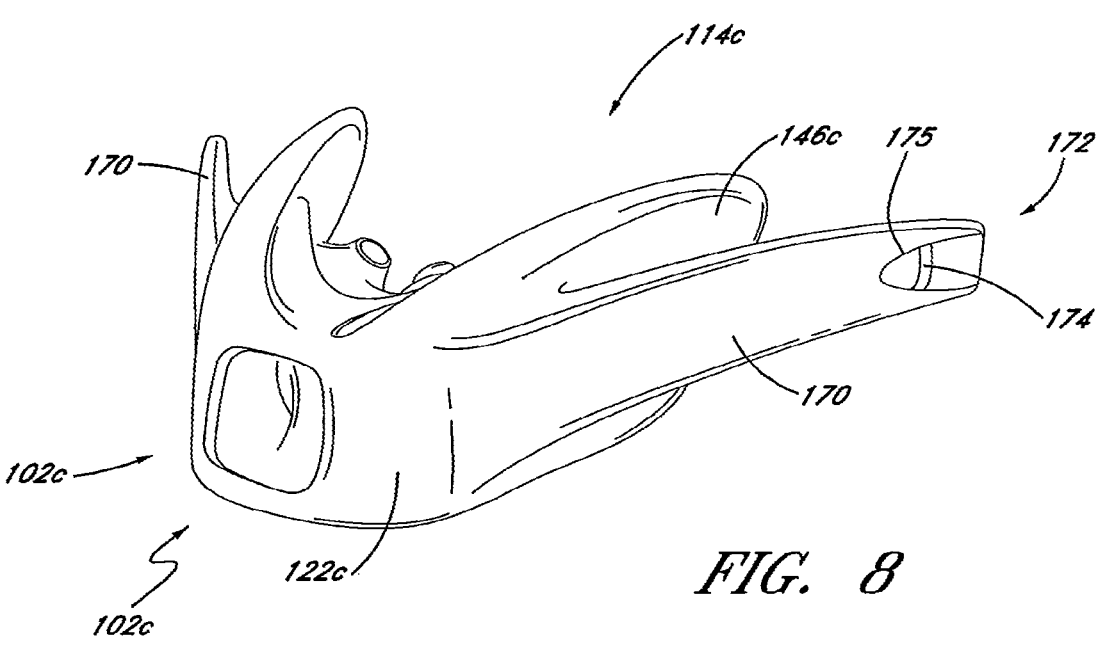
FIG. 8 is a view of a portion of an interface assembly that is arranged and configured in accordance with certain features, aspects and advantages of the present invention.
Figures 9A, 9B, 9C, 9D, 9E, 9F:
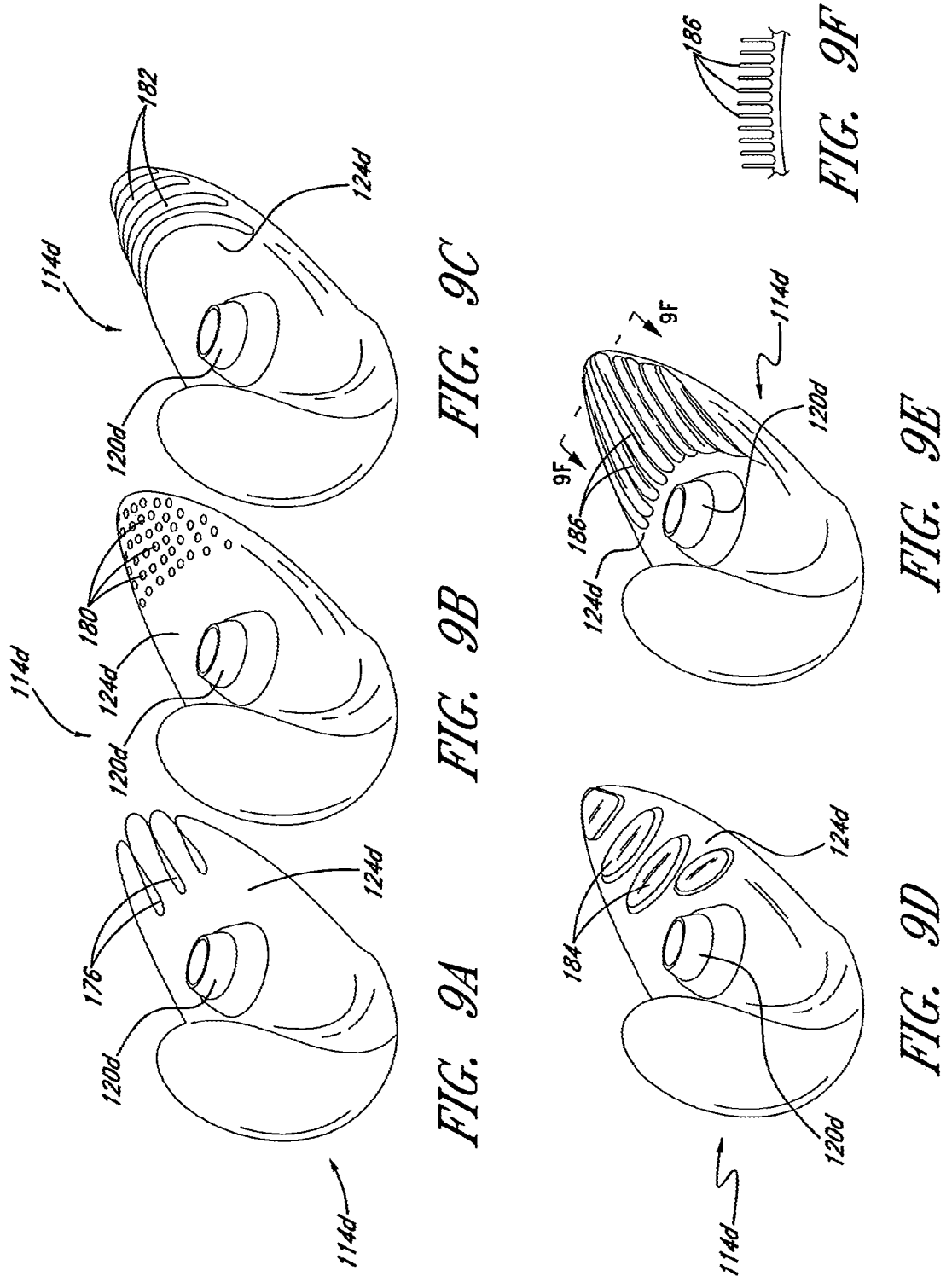
FIGS. 9A-9F are views of portions of an interface assembly that are arranged and configured in accordance with certain features, aspects and advantages of the present invention.

With reference now to FIG. 8, a mask 102c can have a seal 114c that features integrated arms 170. In the illustrated configuration, the arms 170 can extend along an outer portion of the distal wall 122c. With the arms 170 integrated into the seal 114c, the frame 116 can be omitted, integrated directly into the seal 114c or remain a separate supporting element. When integrated into the seal 114c, the mask frame 116 can be defined by a region of increased stiffness (i.e., a region of less suppleness). For example, when integrated into the seal 114c, the mask frame 116 features can be replaced with regions of increased thickness or overmolded characteristics.

In the illustrated configurations, the integrated arms 170 extend proximally from a distal region of the distal wall 122c. Preferably, each end 146c is separated from the associated arm 170 such that the ends 146c can move without significant movement of the overlying portion of the arms 170. In other words, the connection between the arms 170 and the distal wall 122c can terminate distally of the end 146c such that at least a portion of the arm 170 overlies, but is not directly connected to, the proximal end of the distal facing wall 122c.

In the illustrated configuration, an attachment member 172 can be formed at the proximal end of each arm 170. The attachment member 172 can have any suitable configuration and can be used to connect the arms 170 to a strap (not shown) or other headgear assemblies. In the illustrated configuration, the attachment member 172 comprises a post 174 that is positioned within a recess 175. The strap or other headgear can be passed around the post 174 or secured with a hook member to the post 174 for example but without limitation.

FIGS. 9A-9F illustrate seals 114d having differing surface textures along at least a portion of the proximal wall 124d. The surface textures can be positioned along any portion of at least the proximal wall 124d. In some configurations, the surface textures can be positioned along a proximal portion of the proximal wall 124d. In some configurations, the surface textures are only positioned along a proximal portion of the proximal wall. In some configurations, the surface textures can be positioned on other surfaces but, with respect to the proximal wall 124d, the surface textures are only positioned proximally of any nostril locators 120d.

FIGS. 9A-9F illustrated the following surface textures: slots 176; recesses 180; scallops 182; plateaus 184; and ribs 186. Any other suitable surface textures, including shapes, recesses and protrusions, can be provided to the proximal wall 124d of the seal 114d. In some configurations, a combination of surface textures, including but not limited to those described herein, can be used.

In some configurations, the textured portions are positioned outboard of the nostril locators 120d. In some configurations, the textured portions are positioned entirely outboard of the nostril locators 120d. In some configurations, the textured portions can surround, generally surround or be positioned generally adjacent to the nostril locators 120d. In such locations, the textured portions can reduce the contact surface area with the skin of the user while still maintaining an adequate seal against the face of the user. By reducing the contact surface area between the face of the user and the seal 114d, the contact region is perceived by the user to be cooler. Because, in some configurations, other regions besides the regions having the textured surfaces define a primary seal with the face, the textured surfaces can improve comfort without significantly deteriorating the seal present between the seal 114d and the face.

Figure 10:
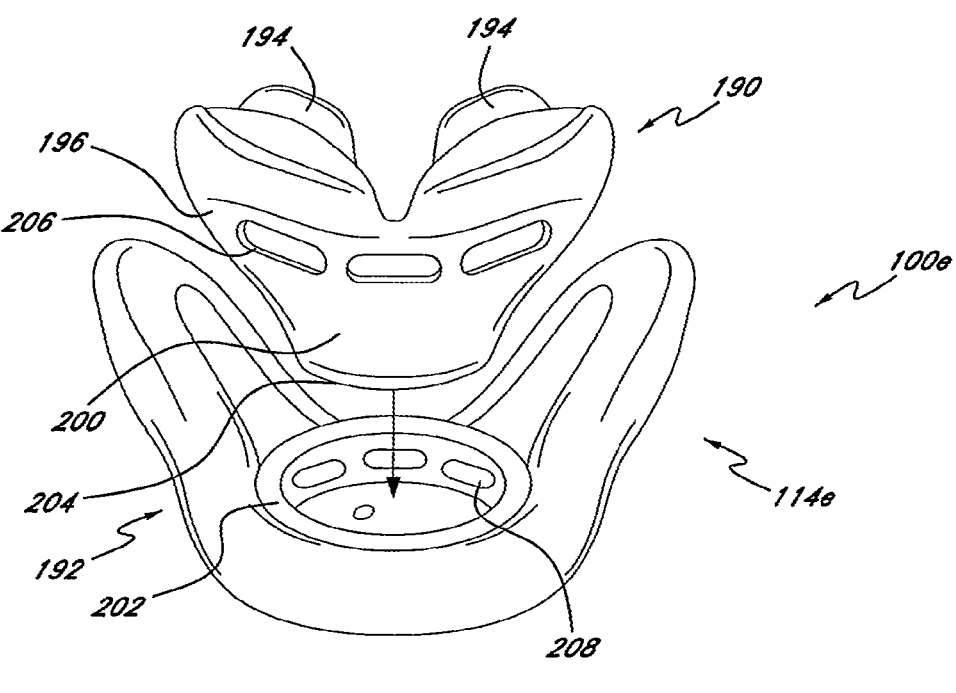
FIG. 10 is a view of a portion of an interface assembly that is arranged and configured in accordance with certain features, aspects and advantages of the present invention.
Figure 11:
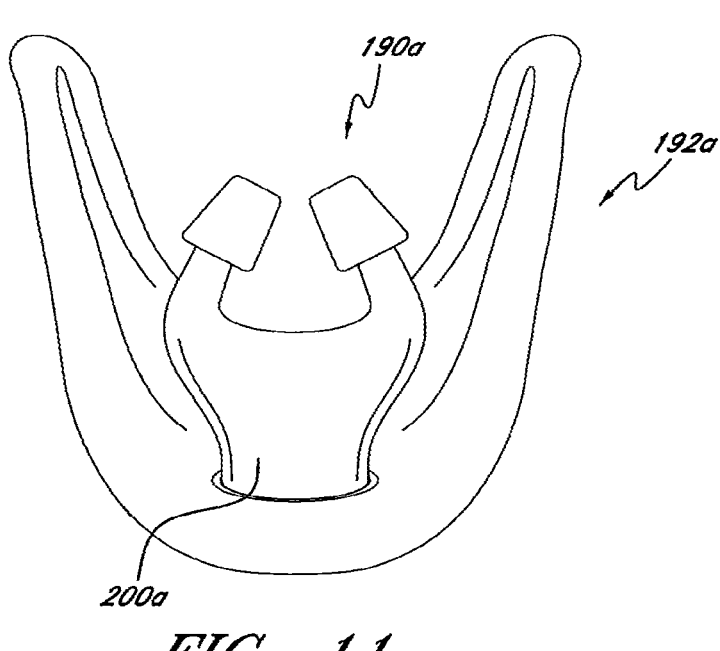
FIG. 11 is a view of a portion of an interface assembly that is arranged and configured in accordance with certain features, aspects and advantages of the present invention.
Figure 12:
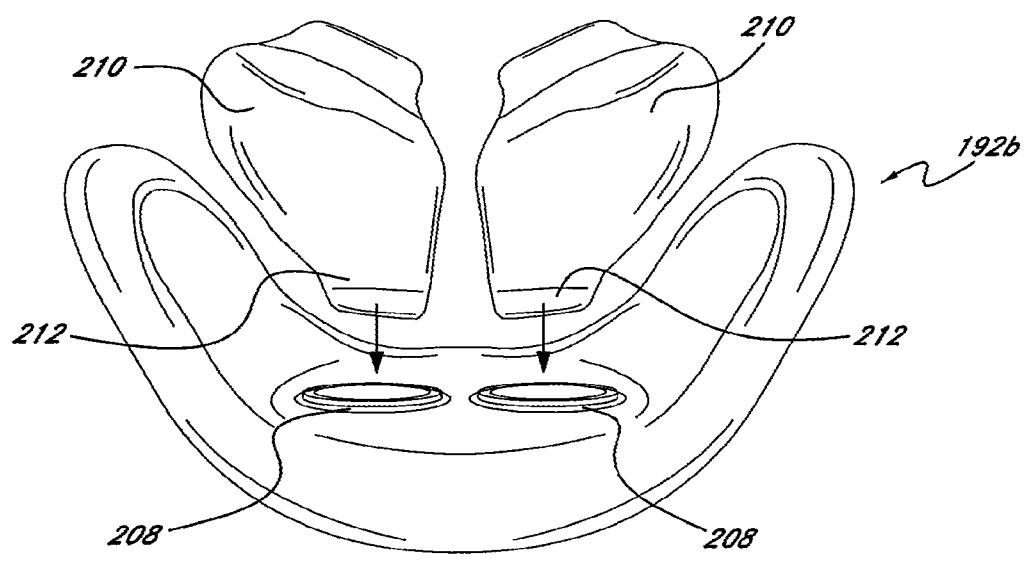
FIG. 12 is a view of a portion of an interface assembly that is arranged and configured in accordance with certain features, aspects and advantages of the present invention.

The interface illustrated in FIGS. 1-4 is a construction that has integrated both the seal 114 and the nostril locators 120 into a single component. With reference now to FIGS. 10-12, the interface also can comprise masks with separable nostril locators and seals. By providing separability between the seal and one or more of the nostril locators, the mask can be better adapted for use by users having different facial geometries. For example, different separable components can have different sizes. In some configurations, the inflating seal can be universal while the nostril locators can be exchanged depending upon the size desired by the user. In some configurations, the seal could be provided in different geometries, such as, for example but without limitation, a wide version and a narrow version.

With reference now to FIG. 10, the illustrated interface 100e comprises a seal 114e with a separable nasal insert 190 and seal member 192. While the seal 114e is formed from more than one component, the seal 114e otherwise can be configured generally in the same manner as the seal 114 shown in FIGS. 1-4 and described above. For example, the seal 114e can be configured with more supple and less supple regions similar to the seals disclosed above.

The nasal insert 190 comprises at least one nostril locator 194. The nostril locators 194 can sit atop a main body 196. In the illustrated configuration, two nostril locators 194 are integrally formed with the main body 196. In some configurations, the two nostril locators 194 can be separable from the main body 196.

The main body 196 comprises a plug portion 200 and the seal member 192 comprises a socket portion 202. The plug portion 200 can be received within the socket portion 202 as indicated by the arrow in FIG. 10. In some configurations, the plug portion 200 locks into position within the socket portion 202. In some configurations, the plug portion 200 is secured by a friction fit within the socket portion 202. Other suitable techniques for securing the plug portion 200 and the socket portion 202 can be used.

A distal end 204 of the main body 196 comprises an inlet opening and, proximally of the inlet opening, the main body 196 comprises one or more openings 206. The inlet opening can be connected to the flexible supply conduit 106. The seal member 192 comprises one or more internal voids or openings 208 and, when the plug portion 200 is positioned within the socket portion 202, the one or more internal voids or openings 208 can be in fluid communication with the one or more openings 206. Thus, in the configuration of FIG. 10, the gases flow from the flexible conduit, into the nasal insert 190 and a portion of the gases flow from the nasal insert 190 into the seal member 192 while a portion of the gases flow from the nasal insert 190 through the nostril locators 194 to the user.

With reference to FIG. 11, a nasal insert 190a and a seal member 192a can combine to define a mask. The nasal insert 190a can have an inlet at a plug portion 200a, which is located at a distal end of the nasal insert 190a. The inlet can be formed by the plug portion 200a. The seal member 192a, however, can have a distal inlet (not shown) that connects directly to a supply conduit (i.e., connects to the supply conduit rather than receiving flow from the nasal insert 190a) and an outlet that connects to the nasal insert 190a. The nasal insert 190a may include but does not require the openings used in the configuration of FIG. 10. Thus, in the configuration shown in FIG. 11, gases are supplied to the seal member 192a first and the seal member 192a passes the gases on to the nasal insert 190a through the inlet at the distal end of the nasal insert 190a prior to the nasal insert 190a passing the gases from the nasal insert 190a to the nostril locators 194a.

With reference now to FIG. 12, a further multi-piece seal construction will be described. The multi-piece construction enables customization of the seal to the user. For example, different size nostril locators can be used with a universal seal member or different size seal members. In addition, nostril locators having differing stiffness or rigidity can be used and/or seal members with different levels of stiffness can be used. In some configurations, the seal member and the nostril locators can be formed of the same material. In some configurations, the seal member and the nostril locators can be formed of differing grades of the same material.

The seal member 192b shown in FIG. 12 comprises one or more outlet openings 208 formed on a proximal surface. In the illustrated configuration, the seal member 192b comprises two openings 208 that receive individual nostril locators 210. The openings 208 can define sockets while distal ends 212 of the nostril locators 210 can define plugs. As illustrated in FIG. 12, the distal ends 212 fit into the openings 208. The nostril locators 210 can be connected to the seal member 192*b* in any suitable manner. In some configurations, the nostril locators 210 can be friction fit into the openings 208. In some configurations, the distal ends 212 and the openings 208 can be configured to connect in only one rotational orientation. In some configurations, the rotational orientation can be varied to customize the fit of the nostril locators 210. In some configurations, the relative rotational orientation between the openings 208 and the nostril locators 210 can be indexable such that the two can be rotationally adjusted and secured in a desired rotational position.

Figure 13:
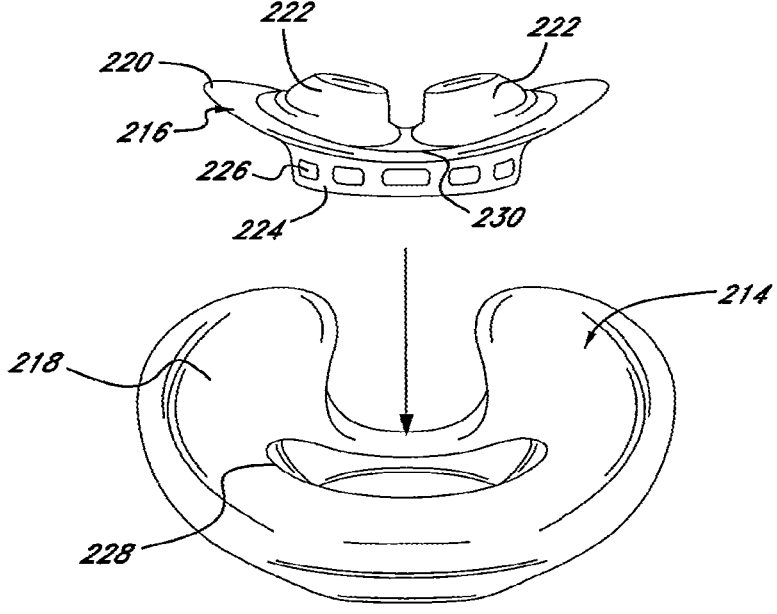
FIG. 13 is a view of a portion of an interface assembly that is arranged and configured in accordance with certain features, aspects and advantages of the present invention.

With reference now to FIG. 13, a seal 214 is illustrated that features a separable nasal insert 216 and seal member 218. The seal 214 can be similar to the construction of any of the configurations described above. In some configurations, however, the nasal insert 216 comprises an auxiliary component 220. As illustrated in FIG. 13, the auxiliary component 220 can be positioned between the one or more nostril locators 222 and a base 224 of the nasal insert 216. In some configurations, a rim 230 can encircle the one or more nostril locators 222 and the auxiliary component 220 can be positioned between the rim 230 and the base 224. In some configurations, the rim 230 can be positioned between the one or more nostril locators 222 and the auxiliary component 220. In the illustrated configuration, the base 224 of the nasal insert 216 can comprises one or more opening 226 but need not.

The seal member 218 can be supple, as described above. In the illustrated configuration, the seal member 218 comprises an opening 228 that receives at least a portion of the nasal insert 216. The opening 228 and the auxiliary component 220 are supple enough to enable the auxiliary component 220 of the nasal insert 216 to be inserted into the pocket defined within the walls of the seal member 218. In some configurations, the opening 228 seals about a portion of the nasal insert 216 between the auxiliary component 220 and the rim 230.

The rim 230 and the auxiliary component 220 can be separated by a gap, a recess, a channel, or a groove, for example but without limitation. The seal member 218 can include a lip that is received within the gap, recess, channel or groove that can be defined between the rim 230 and at least a portion of the auxiliary component 220. In other words, the auxiliary component 220 can overlie, and can be separated from, at least a portion of the rim 230. The gap between the auxiliary component 220 and the rim 230 can be sized and configured to receive at least a portion of the seal 214. In this manner, the seal member 218 and the nasal insert 216 can be secured together, for example but without limitation. Moreover, in the illustrated configuration, the seal member 218 and the nasal insert 216 can be sealed together.

Figure 14A:
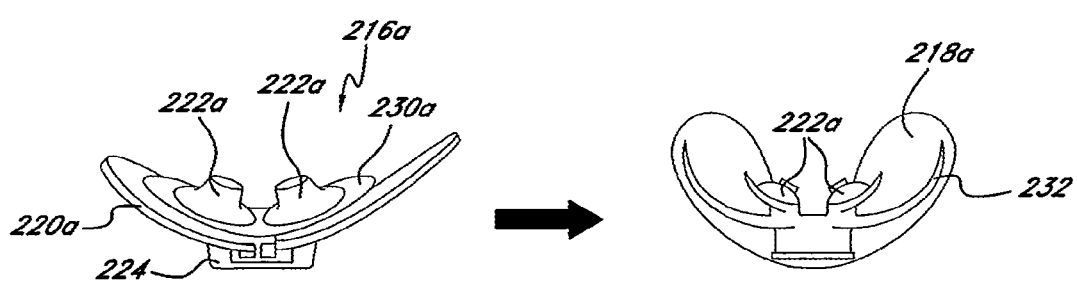
FIG. 14A-14D are views of portions of interface assemblies that are arranged and configured in accordance with certain features, aspects and advantages of the present invention.

With reference now to FIGS. 14A-14D, a sampling of different constructions of auxiliary components will be described. A nasal insert 216*a* is shown in FIG. 14A in which the auxiliary component 220*a* comprises a slightly curved blade member 232. The blade member 232 extends laterally outward beyond the nostril locators 222*a* and laterally outward beyond an outermost extent of the rim 230*a* that generally encircles the nostril locators 222*a*. The blade member 232 can be formed integrally with the nasal insert 216*a* or can be formed separate of the nasal insert 216*a* and secured thereto in any suitable manner. In some configurations, the blade member 232 is formed of silicone. The blade member 232 can be a resilient member that has the ability to bend into a first position and a second position. In some configurations, the blade member 232 can be a member that is bi-directionally stable. In other words, the blade member 232 can assume two distinct positions with sufficient stability to remain at least temporarily in those positions. In some configurations, the blade member 232 has sufficient resilience to assume a first shape or position when the associated seal member 218*a* is underinflated or not inflated. In some configurations, the blade member 232 will bend or deflect when the associated seal member 218*a* is inflated for use. Such a configuration is shown in FIG. 14A in which the outermost portions of the blade member 232 have been deflected upwardly.

As shown in FIG. 14A, the blade member 232 provides added material that contacts one or more inner surface of a seal member. The blade member 232 can be configured to urge the seal member 218*a* into an open position to assist with fitting of the mask on the face of the user by can deflect out of the way during use of the interface by the user. By slightly opening the mask, the nostril locators 222*a* can be mated with the nostrils more easily. Once gas pressure is supplied to the seal member 218*a*, the seal member will inflate and balloon into sealing engagement with the face of the user. Preferably, the blade member 232 is supple enough that, once the seal member 218*a* starts to inflate, the blade member 232 can bend and conform to the shape of the seal member 218*a* such that the seal member 218*a* can inflate and seal around the nose of the user.

Figure 14B:
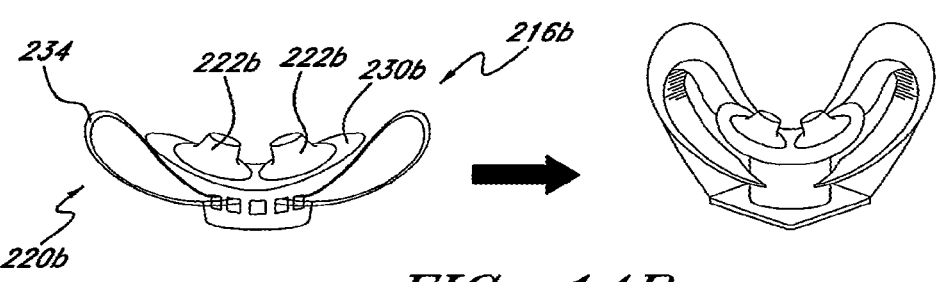
Figure 14B:
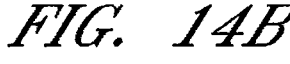

FIG. 14B illustrates a nasal insert 216*b* that is similar in some respects to the nasal insert 216*a* shown in FIG. 14A. A rim 230*b* of the nasal insert 216*b* in FIG. 14B comprises a loop member 234. The loop member 234 is similar to the blade member 232 in some respects; however, the loop member 234 extends both proximally and distally while also extending laterally outward. In other words, as apparent from comparing FIG. 14A with FIG. 14B, while the blade member 232 is generally a flat dish-shaped component in FIG. 14A, the loop member 234 is less flat and extends both fore and aft. As such, the loop member 234 facilitates manipulation of the proximal portion of the associated seal member 218*b* but also facilitates manipulation of the distal portion of the seal member 218*b*. In other words, whereas the blade member 232 contacts the inner surface on the distal portion of the seal member, the loop member 234 is capable of contacting the inner surfaces on the proximal and distal portions of the seal member 218*b*.

With continued reference to FIG. 14B, the loop member 234 extends laterally outward of the nostril locators 222*b* and outward beyond an outermost extent of the rim 230*b*. The loop member 234 can be formed integrally with the nasal insert 216*b* or can be formed separate of the nasal insert 216*b* and secured thereto in any suitable manner. In some configurations, the loop member 234 can be formed of silicone.

By contacting the inner surfaces of the seal member 218*b*, the loop member 234 places the seal member 218*b* in an opened position prior to inflation of the seal member 218*b* and provides an initial shape to the deflated seal member 218*b*. Once gas pressure is supplied to the seal member 218*b*, the seal member 218*b* will inflate and balloon into sealing engagement with the face of the user. Preferably, the loop member 234 is supple enough that, once the seal member 218*b* starts to inflate, the loop member 234 can bend and conform to the shape of the seal member 218*b* such that the seal member 218*b* can inflate and seal around the nose of the user. In some configurations, the loop member 234 can toggle between two positions. In some configurations, the loop member 234 can be structured to simply deflect out of the opened or first position as the seal inflates but resume the opened or first position when the seal once again deflates.

Figure 14C:
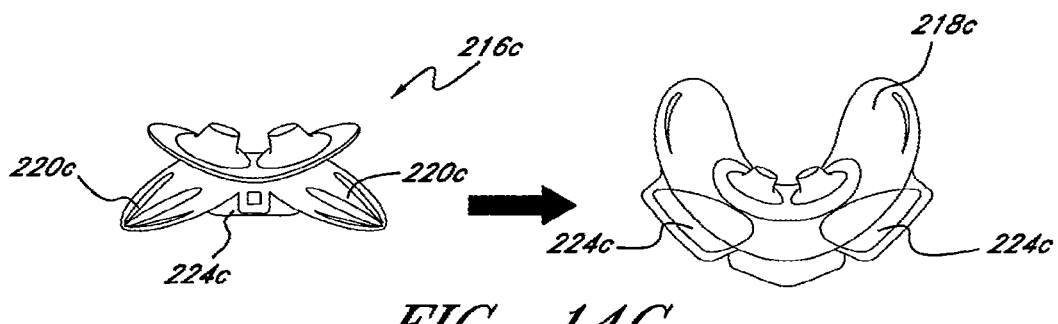

FIG. 14C illustrates a nasal insert 216*c* having an auxiliary component 220*c* that is inflatable. The auxiliary component 220*c* comprises one or more stabilizers 236. The stabilizers 236 can have one or more outer wall and can be inflatable. Thus, an inner pocket defined within the stabilizer 236 can communicate with a gas source, such as the flow through the associated seal member 218*c*. In the illustrated configuration, the stabilizers 236 can be connected to the base 224*c* of the nasal insert 216*c*. The ballooning stabilizers 236 can provide a force to urge the proximal surface of the seal member toward the face of the user when at operating pressures. Thus, different from the loop member 234 and the blade member 232, the ballooning stabilizers 236 do not serve to hold the uninflated mask in an open position; the stabilizers 236 provide an improved sealing force during use.

Figure 14D:
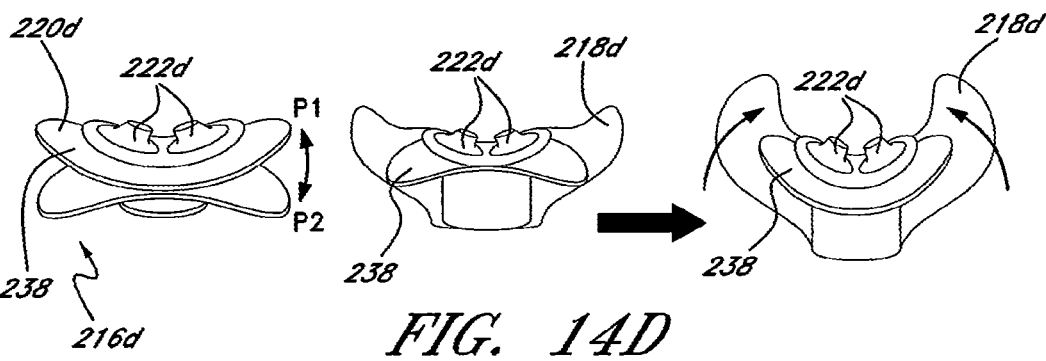

With reference to FIG. 14D, a nasal insert 216*d* is illustrated with an auxiliary component 220*d* that can flex between a first position P1 and a second position P2. The auxiliary component 220*d* can comprise a dish member 238 that is stable in the first position P1 and in the second position P2. In some configurations, the dish member 238 can flip between the first position P1 and the second position P2 but will return to the first position P1 with the application of minimal force. As shown in FIG. 14D, the dish member 238 can be flexed into the second position P2 for donning of the mask. With the dish member 238 in the second position P2, the seal member 218*d* can be held in the open position. Once positioned as desired on the user, a slight urging of the dish member 238 toward the face of the user causes the dish member 238 to pop back into the first position P1, which allows the seal member 218*d* to move to a more closed position.

Accordingly, to don the mask with the assembly illustrated in FIG. 14D, the dish member 238 can be flexed from the first position P1 to the second position P2. The dish member 238 temporarily is stabilized in the second position as the mask is being positioned such that the nostril locators 222*d* can be positioned within the nostrils of the user. As the mask is brought into engagement with the face of the user, the forces applied through the seal member 218*d* transfer to the dish member 238, which pops back or otherwise returns to the first position P1. With the dish member 238 in the first position, the seal member 218*d* can close around the tip of the nose of the user, which allows the mask with the assembly illustrated in FIG. 17 to seal around the tip of the nose of the user.

Figure 15A:
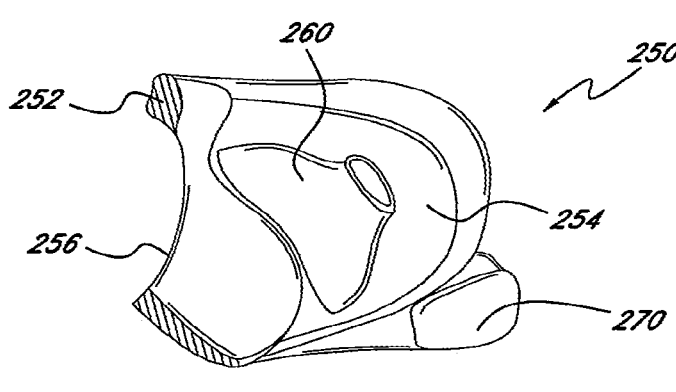
FIGS. 15A-15D are views of a portion of an interface assembly that is arranged and configured in accordance with certain features, aspects and advantages of the present invention.

With reference now to FIG. 15A, a portion of a seal member 250 is shown. The seal member 250 can be configured in accordance with any combination of features of any of the constructions described within this specification, for example but without limitation. The seal member 250 can comprise a distal wall 252 and a proximal wall 254. An opening 256 can be defined within the distal wall 252. A supply of gases can pass into the seal member 250 through the opening 256.

As shown in FIG. 15A, the distal wall 252 can have a thicker cross-section, for example, relative to the proximal wall 254. The thicker cross-section provides increased rigidity to the distal wall 252 relative to the proximal wall 254. In some configurations, the thickness of the walls can be the same while the material used has an increased rigidity. In some configurations, both the thickness and the rigidity of the material can be used to provide differing degrees of rigidity.

In the illustrated configuration of FIG. 15A, a nostril locator 260 can be positioned along the proximal wall 254. The illustrated nostril locator 260 can generally taper such that it narrows toward a proximal opening 262. As such, the proximal opening 262 may have a smaller diameter than a distal opening into the nostril locator 260. Generally speaking, the nostril locator 260 can taper in a proximal direction.

Figures 15B, 15C:
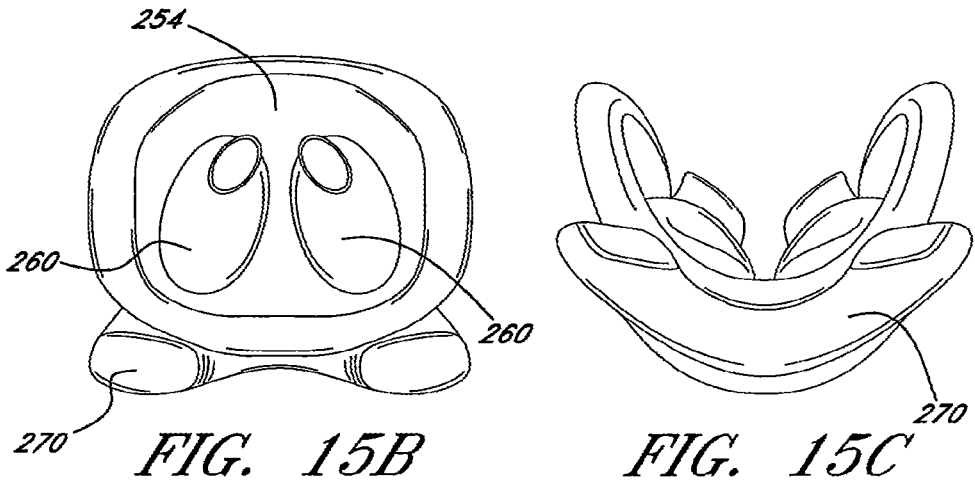

To improve lateral stability of the mask assembly, outriggers or other support structures can be used. In the configurations illustrated in FIGS. 15A-15D, however, the support structures are shown integrated into the structure of the seal member 250 itself. With reference to FIGS. 15A-15C, a support structure 270 is shown that is integrated into the seal member 250. With the integrated support structure 270, the mask is more comfortable than other masks that might use separate support structures that are more rigid than the seal member. Moreover, because the support structure 270 can be directly adjacent to the user's face, the integrated design provides for better support to the scaling member 250.

The illustrated support structure 270 can be one or more thickened regions. For example, where the seal member 250 if formed of silicone, the support structure 270 can be a thickened region of silicone. In some such configurations, the support structure 270 can be molded into the seal member 250. In some configurations, foam could be injected or inserted into the support structure 270. For example, in some such configurations, the support structure 270 can be formed with a hollow region (or material could be removed) and the region can be filled with any desired gel or foam substance. In some configurations, the support structure 270 can be formed of silicone and the hollow region can be filled with a different grade of silicone. Such composite support structures can reduce the weight of the seal and mask assembly.

By molding the support structure 270 into the seal member 250, the support structure can flex with the seal member 250. Flexing of the seal member 250 allows the seal member 250 to better fit different face shapes. Additionally, the support structure 270 can move with the seal member 250 and the seal member 250 can sit closer to the face. Furthermore, integration of the support structure 270 into the seal member 250 simplifies manufacture of the mask because, by integrating the support structure 270 into the seal member 250, the support structure is not separately formed or formed by an overmolding process. Moreover, the integration reduces the weight of the assembly while also facilitating a reduced size.

Figure 15D:
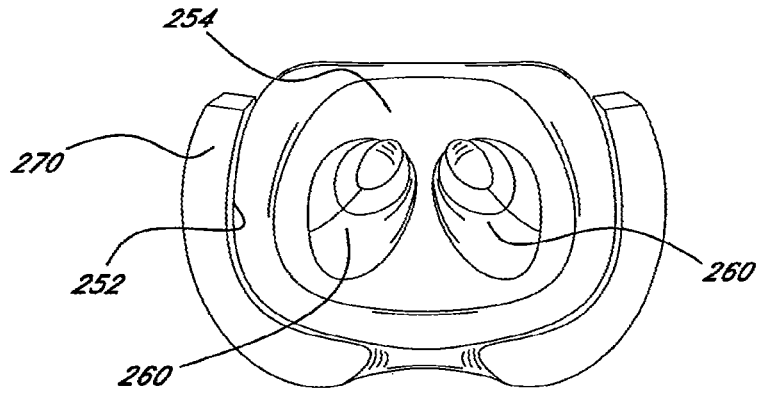

With reference to FIGS. 15A-15C, the illustrated support structure 270 is a crescent shaped member that generally underlies the seal member 250. With reference to FIG. 15D, in some configurations, the support structure 270 can wrap upward along one or more of the outer (distal) side walls 252. Thus, as shown, the support structure 270 can be provided in a variety of shapes. The shape of the support structure 270 can be tailored to provide support to the seal member 250 wherever desired because the support structure 270 can be molded in an integrated construction. While the configuration of FIGS. 15A-15C illustrate a structure that provides support just above a lip region of a user, the configuration of FIG. 15D reassigns the support to a check region rather than the fairly narrow region above the lips and below the nose. Thus, in the configuration of FIG. 15D, the support is shifted to the outside toward the checks, away from the upper lip. In some configurations similar to the configuration of FIG. 15D, the support remains on about the bottom half of the seal member 250 even though the support structure 270 wraps vertically upward along the sidewall. By shifting the support structure 270 location, the comfort of the seal member 250 can be improved while also improving the performance of the seal member 250.

Figure 16:
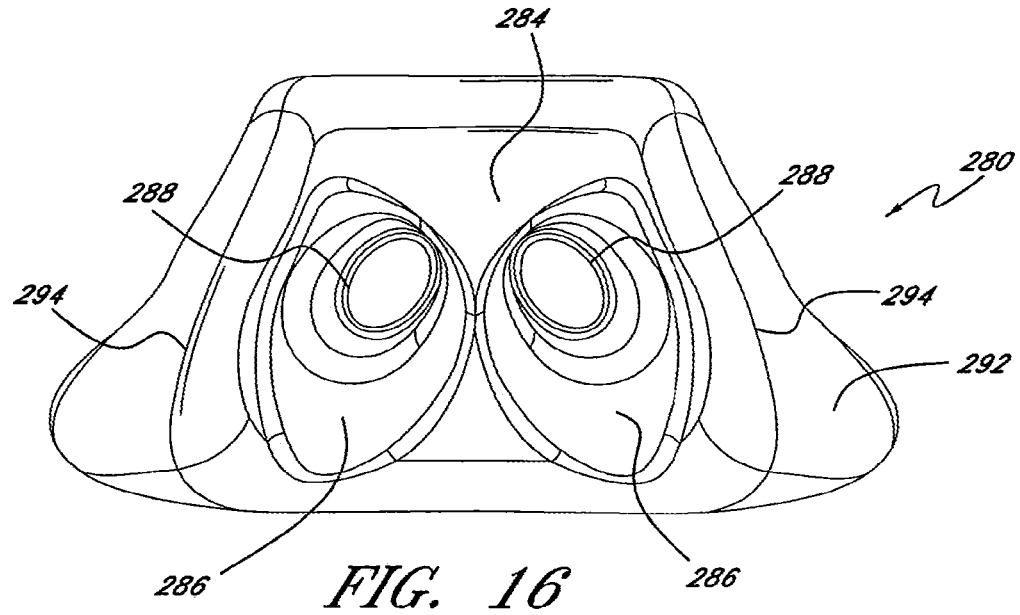
FIG. 16 is a rear view of a portion of an interface assembly that is arranged and configured in accordance with certain features, aspects and advantages of the present invention.
Figure 17:
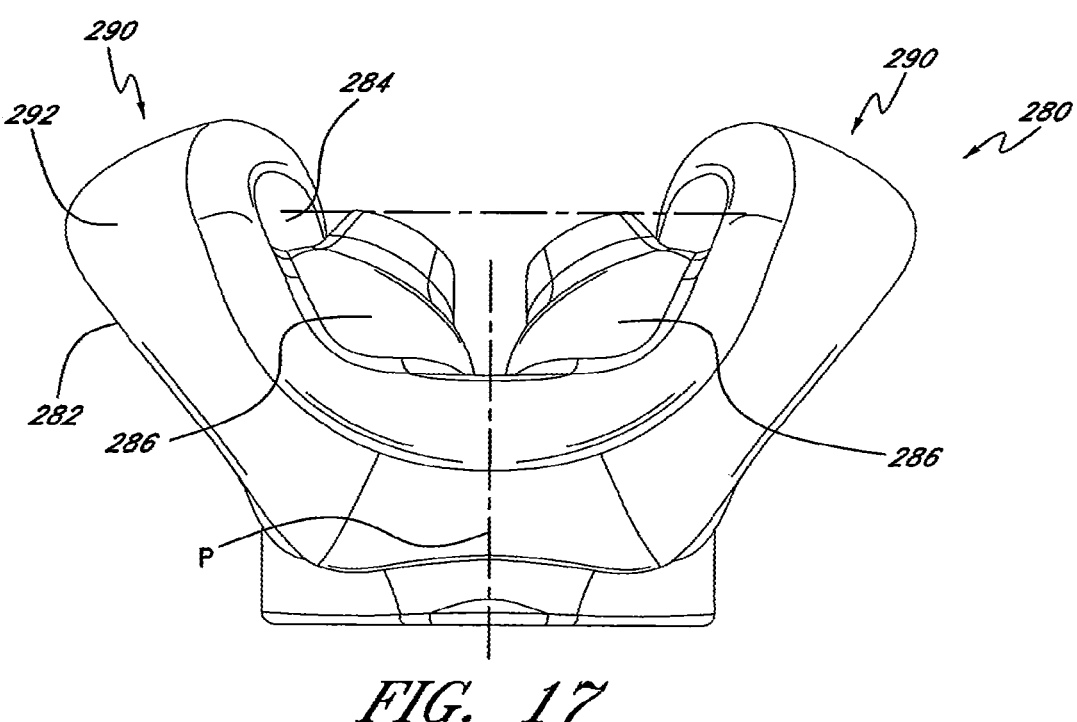
FIG. 17 is a bottom view of the portion of the interface assembly of FIG. 16.
Figure 18:
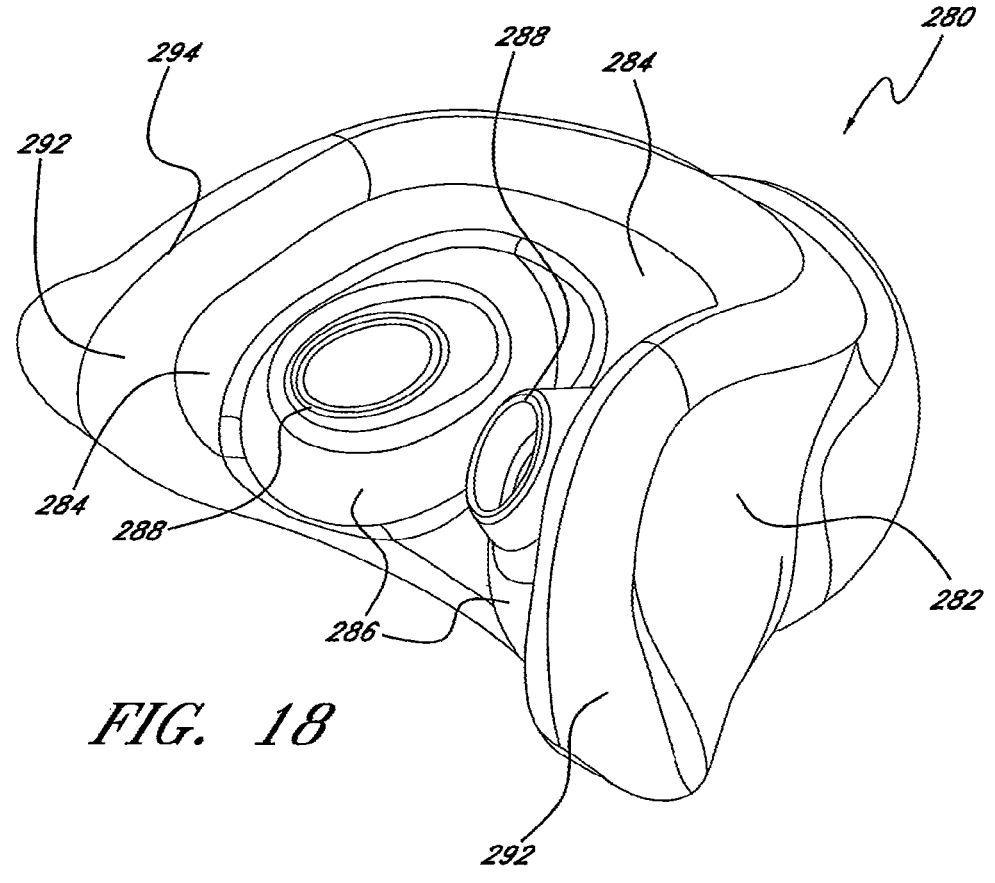
FIG. 18 is a perspective view of the portion of the interface assembly of FIG. 16.

With reference now to FIGS. 16-18, another mask seal member 280 is illustrated. The mask seal member 280 comprises a distal wall 282 and a proximal wall 284. One or more nostril locators 286 can be positioned on at least a portion of the proximal wall 284. The nostril locators 286 can have any suitable configuration. In some configurations, the nostril locators 286 taper upwardly to openings 288.

As illustrated in FIG. 17, the proximal wall 284 wraps proximally around the nostril locators 286 Moreover, the illustrated nostril locators 286 span a portion of the proximal wall 284 that is generally normal to a vertical bisecting plane P as well as a portion of the proximal wall that wraps proximally. Other configurations are possible. In the illustrated configuration, the proximal wall 284 extends more proximally than the proximal most portion of the nostril locators 286. Because the seal member 280 has laterally extending portions 290 that wrap proximally, the laterally extending portions 290 may hold the nostril locators away from the nares on flatter user face profiles. To help provide improved flexibility, the seal member 280 can be reinforced in regions closer to the nose compared to the checks.

With reference to FIG. 16, the seal member 280 can comprise a marginal surface 292 that connects the proximal wall 284 to the distal wall 282. The marginal surface 292 in the illustrated configuration is wider at the bottom than at the top. As illustrated, the marginal surface can provide a wider portion on the bottom of the illustrated seal member 280. The seal member 280 can have a thicker wall in the bottom corners while the proximal wall 284 can have a reduced thickness in the region surrounding or at least partially surrounding the nostril locators 286. The thicker region of the bottom corners can extend upward and follow the generally vertical line illustrated in FIG. 17.

While a majority of the entire seal member 280 can be configured to balloon, the thicker regions can be configured to balloon less than the regions with a reduced thickness. The thicker regions can help control ballooning such that the proximal surface experiences a majority of the ballooning compared to the marginal surface 292 and the distal surface 282. Thus, the region surrounding the nostril locators 286 can balloon more while the lower corners balloon less, which increases comfort and improves sealing of the mask.

With reference again to FIG. 3, the nostril locators 120 typically are configured to be positioned within the nares. In order to fit within the nares of the user, the nostril locators 120 can be stiff enough to resist crushing during fitting and use. As such, the proximal ends of the nostril locators 120 have been discovered to slightly pinch the septum or otherwise reduce the comfort of the user. Accordingly, removing some of the rigidity of the nostril locators 120, and especially of the proximal ends of the nostril locators 120 and/or in a transition location between the nostril locators 120 and surrounding structure (described below with reference to FIGS. 29-42), can be desirable.

Figure 19:
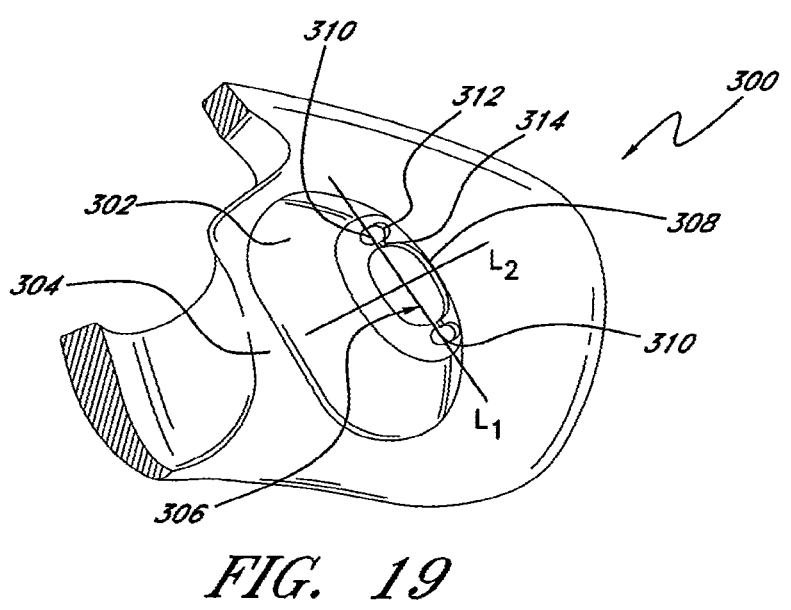
FIG. 19 is a view of a portion of an interface assembly that is arranged and configured in accordance with certain features, aspects and advantages of the present invention.
Figures 20A, 20B, 20C:
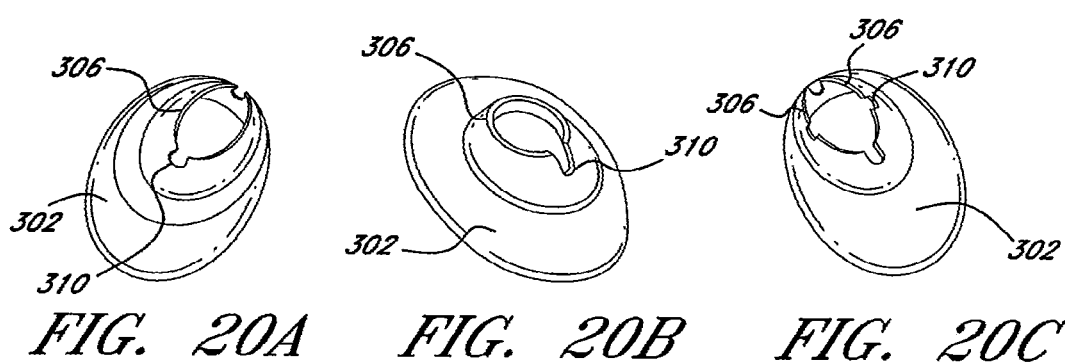
FIGS. 20A-20E are views of portions of interface assemblies that are arranged and configured in accordance with certain features, aspects and advantages of the present invention.
Figures 20D, 20E:
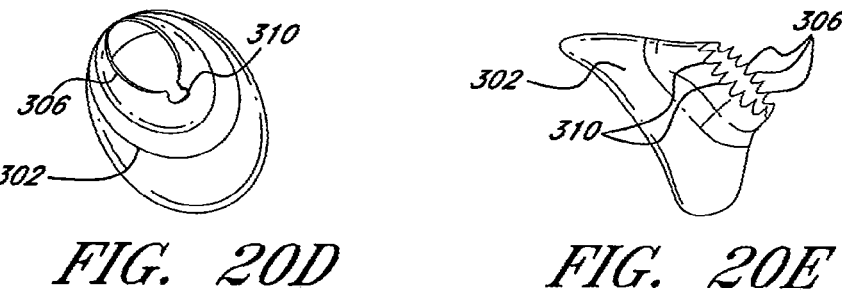

With reference now to FIG. 19, a sealing member 300 is shown in cross-section. A nostril locator 302 is shown extending from a proximal surface 304. The nostril locator 302 can include an opening 306. In the illustrated configuration, the opening 306 can be defined by a rim 308. The rim 308 preferably includes at least one interruption 310. With reference to FIG. 19, the illustrated interruptions 310 comprise a larger opening 312 that is connected to a slot 314 that intersects with the rim 308. In the illustrated configuration, the rim 308 includes two interruptions 310. The interruptions 310 are positioned to be at the top and the bottom of the opening 306 in the illustrated configuration. In other words, when positioned in the nares of the user, the interruptions 310 facilitate flexure in a lateral direction in the configuration illustrated in FIG. 19.

In some configurations, the rim 308 that defines the opening 306 is generally elliptical and includes a longer axis L1 and a shorter axis L2, as shown in FIG. 19. In such configurations, the interruptions 310 can be intersected by the longer axis L1. In some configurations, one or more interruption 310 can be positioned along the portion of the rim 308 that is above the shorter axis L2. For example, a single interruption 310 can be positioned on the upper side of the shorter axis L2. In some such configurations, the single interruption 310 can be positioned closer to the apex of that portion of the elliptical opening 306. In some such configurations, the single interruption 310 can be intersected by the longer axis L1. In some such configurations, the single interruption 310 can be centered upon the longer axis L1.

With continued reference to FIG. 19, the interruptions 310 define recesses into the nostril locators 302 that extend from the rim 308 into the material of the nostril locators 302. The interruptions 310 can extend any suitable distance along the length of the nostril locator 302. The length preferably is not so long as to create a leak path but long enough to allow some radial relief to the rim 308. As the length of the interruptions 310 increases, the stiffness of the nostril locator 302 decreases.

With reference to FIGS. 20A-20E, other configurations of interruptions 310 are illustrated. As illustrated, the interruptions 310 can have many different shapes and can be moved away from a region of the nostril locators 302 that will contact the septum. As illustrated, the interruptions 310 can be as few as one or as many as desired. In some configurations, the interruptions 310 result in a serrated end to the nostril locator 302. Other configurations also are possible.

Figure 21:
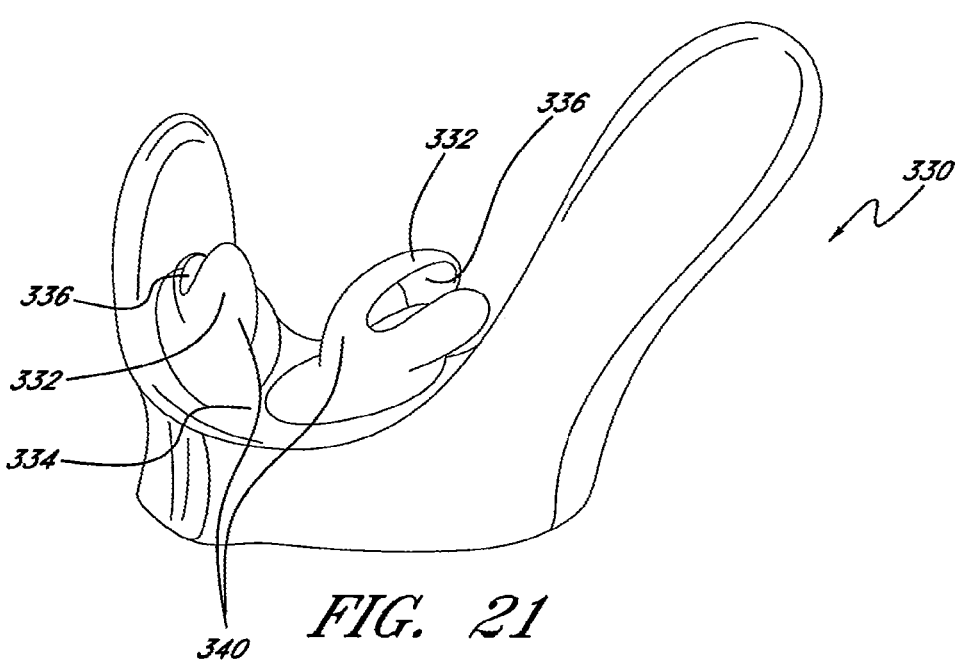
FIG. 21 is a view of a portion of an interface assembly that is arranged and configured in accordance with certain features, aspects and advantages of the present invention.
Figure 22:
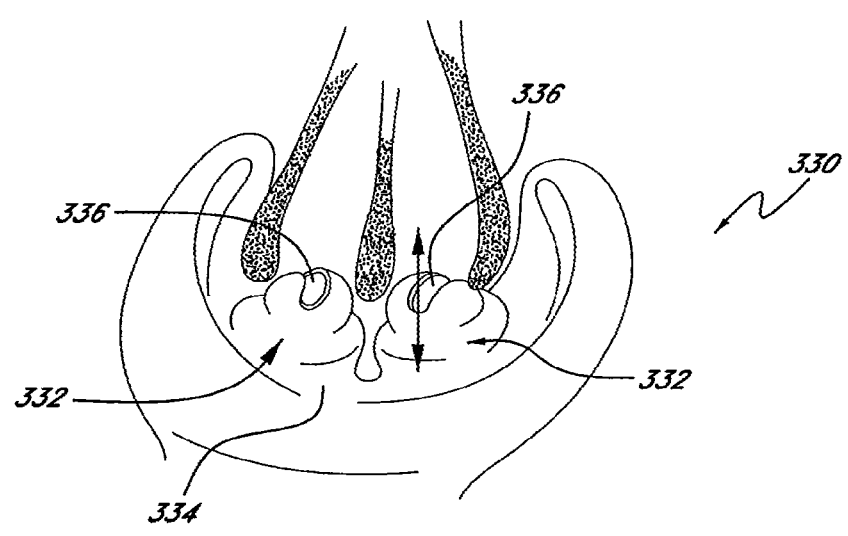
FIG. 22 is a view of a portion of a nasal cavity and a portion of an interface assembly that is arranged and configured in accordance with certain features, aspects and advantages of the present invention.

With reference now to FIGS. 21 and 22, a sealing member 330 is illustrated. The sealing member 330 can have features, aspects and characteristics in common with any other configuration described herein. In the illustrated configuration, the sealing member 330 comprises at least one flexible prong 332. In some configurations, the scaling member 330 can comprise two flexible prongs 332. The flexible prongs 332 comprise a distal end that is connected to a proximal surface 334. The flexible prongs 332 can extend generally proximally from the proximal surface 334. The flexible prongs 332 can have one or more opening 336 that are positioned generally at a proximal end of the prongs 332. In the illustrated configuration, the opening 336 can form a slit that extends generally vertically through the proximal most end.

The prongs 332 preferably comprise a stalk 340 that extends generally between the proximal surface 334 and the opening 336. The stalk 340 can be configured to roll or otherwise deflect with ease. For example, a cross-sectional thickness of the material used to form the sealing member 330 and/or the flexible prongs 332 can be reduced that connects at least a portion of the prongs 332 to the sealing member 330. In some configurations, a different material or a different grade of material can be used to provide increased mobility to the prongs 332.

In the illustrated configuration, as shown by comparing FIG. 21 and FIG. 22, the prongs 332 can be configured to telescope or extend/retract. By configuring the prongs 332 to extend, the prongs 332 can have increased flexibility. As illustrated, the prongs 332 can compress along the axial direction. By compressing, the prongs 332 can improve comfort when sealing against the nares of the user.

In some configurations, the prongs can be configured with a bellows-type shape. The bellows-type shape can provide axial compressibility. The pleated appearance of the bellows-type shape can be formed along all of the stalk 340 or just a portion of the stalk 340. By providing the bellows-type shape, the stalk 340 also can allow the proximal end of the prongs 332 to wobble about the distal end of the prongs 332. In other words, the proximal end of the prongs 332 can bend in all directions without rotation of the prongs 332.

With reference now to FIGS. 23A-23C, a portion of a sealing member 350 is shown. In some configurations, the sealing member 350 includes nostril locators 352 similar to those described above. At least a proximal portion of the nostril locators 352 can be partially or fully covered with an end member 354, as shown in each of FIGS. 23A-23C. The end members 354 can be formed of a material that is as soft as, or softer than, the material of the nostril locator 352. In some configurations, the end members 354 can be partially or fully formed of a softer silicone material. In other words, the end members 354 can be used to provide increased comfort by being positioned over the proximal end of the nostril locators 352.

The end member 354 can define openings 356 through which airflow from the nostril locator 352 can pass. In the illustrated configurations, the end members 354 have a rounded appearance. The softer material and the rounded shape facilitate rolling around the axis of the nostril locator 352. The underlying nostril locator 352 can be sufficiently rigid to provide the structure while the cap formed by the end member 354 can improve the comfort. In some configurations, the proximal end of the nostril locator 352 can be enclosed with perforations or laterally extending openings to allow air to flow out of the nostril locator while the soft end member creates a seal with the nares of the user. In addition, in some such configurations, the end member 354 can have a larger outer diameter than the nostril locator 352 such that the nostril locator 352 can have improved flexibility while the end member provides an effective sealing component.

With reference now to FIG. 24, a further seal member 360 is illustrated. The seal member 360 includes a multiple wall nostril locator 362. In the illustrated configuration, the nostril locator 362 comprises a thin outer wall 364 and a thicker inner wall 366. In some configurations, the outer wall 364 is spaced from the inner wall 366 such that the two walls are capable of relative movement. In some configurations, the inner wall 366 can terminate within the outer wall 364. In other words, the outer wall 364 may extend further proximally relative to the inner wall 366.

The inner wall 366 can comprise a foam or gel insert, for example but without limitation. The inner wall 366 underlies and supports the outer wall 364. Thus, with the support of the separately formed inner wall 366, the outer wall 364 could be formed of a very thin layer. In some configurations, the outer wall 364 can be a very thin silicone wall that is intermittently or substantially completely supported by the inner wall 366, which can be a much softer material than the outer wall 364.

Figure 25A:
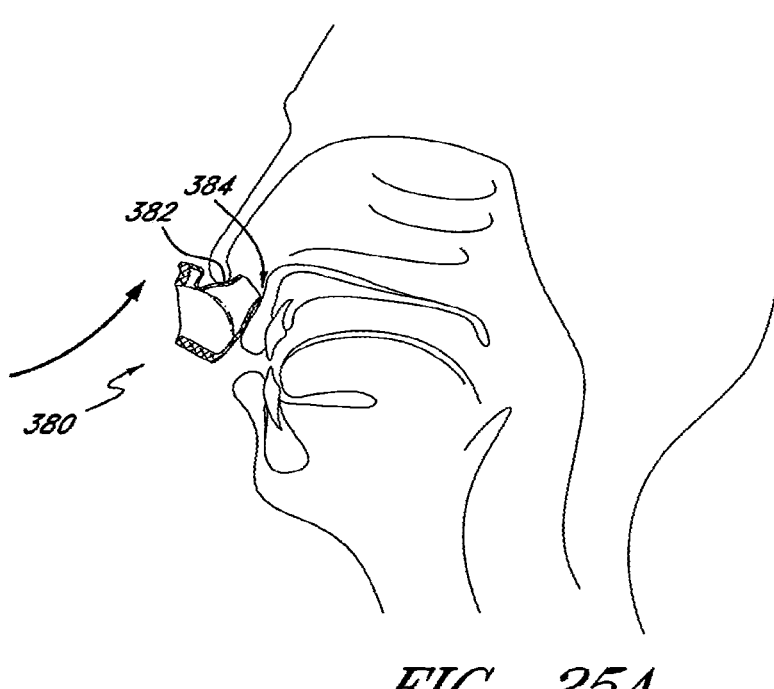
FIGS. 25A and 25B are views of a prior interface assembly and an interface assembly arranged and configured in accordance with certain features, aspects and advantages of the present invention.
Figure 25B:
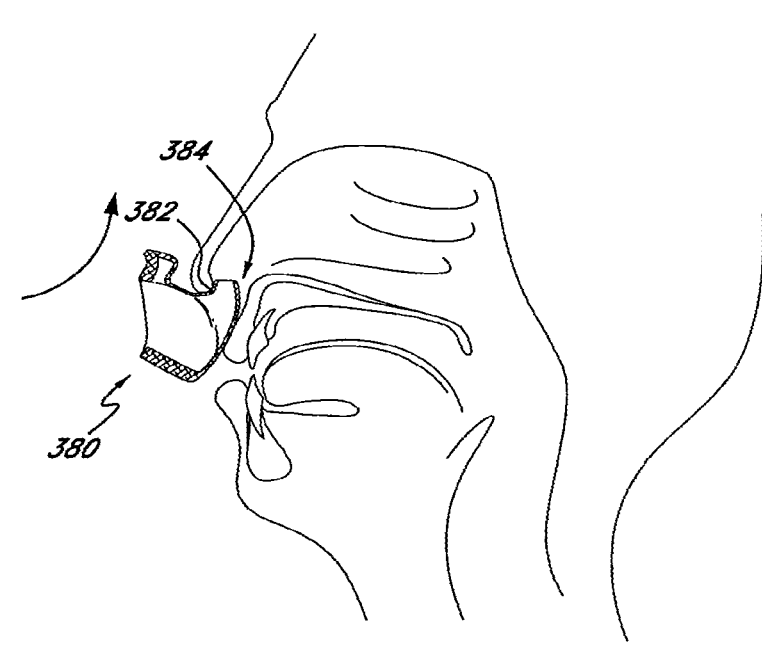

With reference now to FIGS. 25A and 25B, a seal member 380 is illustrated therein. The seal member 380 can include one or more nostril locators 382. In some configurations, the seal member 380 can be configured such that the nostril locators 382 direct the airflow in a more upward direction. With reference to FIG. 25A, the nostril locators 382 are shown directing the airflow more rearwardly when compared to the nostril locators 382 shown in FIG. 25B. By raising the rearmost wall of the nostril locators (see 384), for example, the trajectory of the airflow can be altered to a more upwardly directed flow. In some configurations, the nostril locators are configured such that the resultant airflow is more upwardly and forward. By redirecting the airflow in this manner, the airflow is not blown straight into the nose, which improves the comfort to the user. In some configurations, the nostril locators 382 can be positioned on a ball joint, for example but without limitation, such that the air flow can be tuned by the user as desired.

Figures 26, 27, 28:
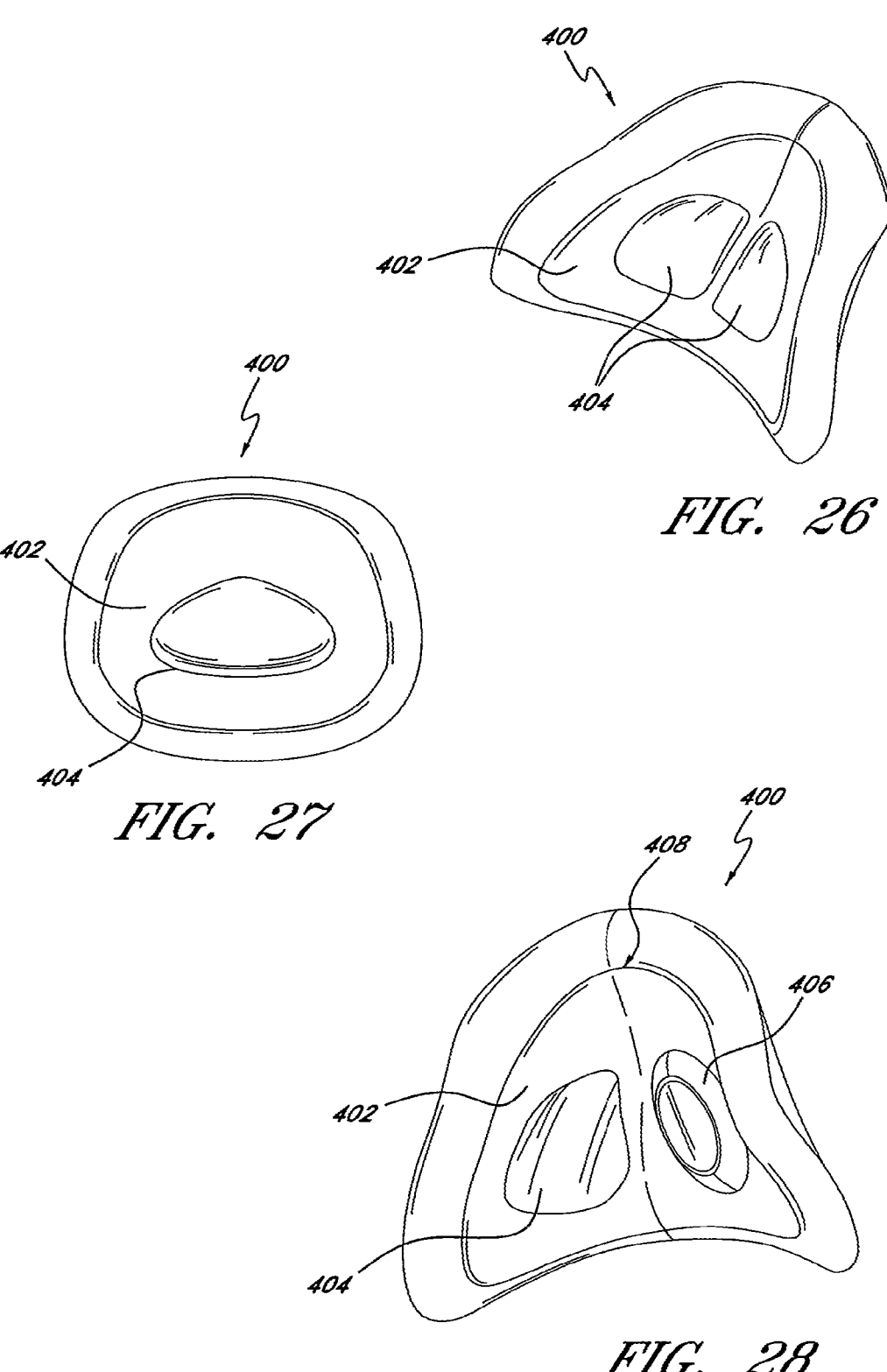
FIG. 26 is a view of an interface assembly that is arranged and configured in accordance with certain features, aspects and advantages of the present invention.
FIG. 27 is a view of another interface assembly that is arranged and configured in accordance with certain features, aspects and advantages of the present invention.
FIG. 28 is a view of another interface assembly that is arranged and configured in accordance with certain features, aspects and advantages of the present invention.

With reference now to FIG. 26, the illustrated seal member 400 can be structured in any configuration described above. The configuration illustrated, however, features a proximal surface 402 that omits one or both nostril locators. In the illustrated configuration, one or more of the nostril locators is replaced by an opening 404 that is formed in the proximal surface 402. Thus, the nostrils of the user can simply overlie an opening 404 that is formed in the proximal surface. The configuration of FIG. 27 shows a single opening 404 that can underlie one or both nostrils of the user while the configuration of FIG. 28 also shows a single protrusion 406 that can help indicate to the user when the mask is properly located under the nose. With reference to FIG. 28, in some configurations, the tip of the nose can sit at the crossing 408 of the two facet lines. The protrusion 406 can be a short nostril locator, a complete nostril locator or any other suitable structure to help the user confirm a desired placement of the mask sealing member relative to the nostrils. In some configurations, the nose fits into or around the opening and the seal member can balloon around the nose of the user. For example, the tip of the nose can go into the opening or the opening can sit under the tip of the nose to provide seal. The ballooning improves sealing of the seal member, especially where nothing extends into the nares of the user.

With reference now to FIGS. 29-42, a further interface assembly 420 is illustrated that is arranged and configured in accordance with certain features, aspects and advantages of the present invention. The interface assembly 420 generally comprises a frame or body 422 and a seal 424. The seal 424 can be removably secured to the frame 422 for use. In some configurations, multiple seals 424 can be provided for connection to the frame 422, which can vary in size, shape, softness or any other desirable characteristic. In the illustrated configuration, the frame 422 provides attachment points for headgear or the like. Other configurations are possible.

Figures 29, 30:
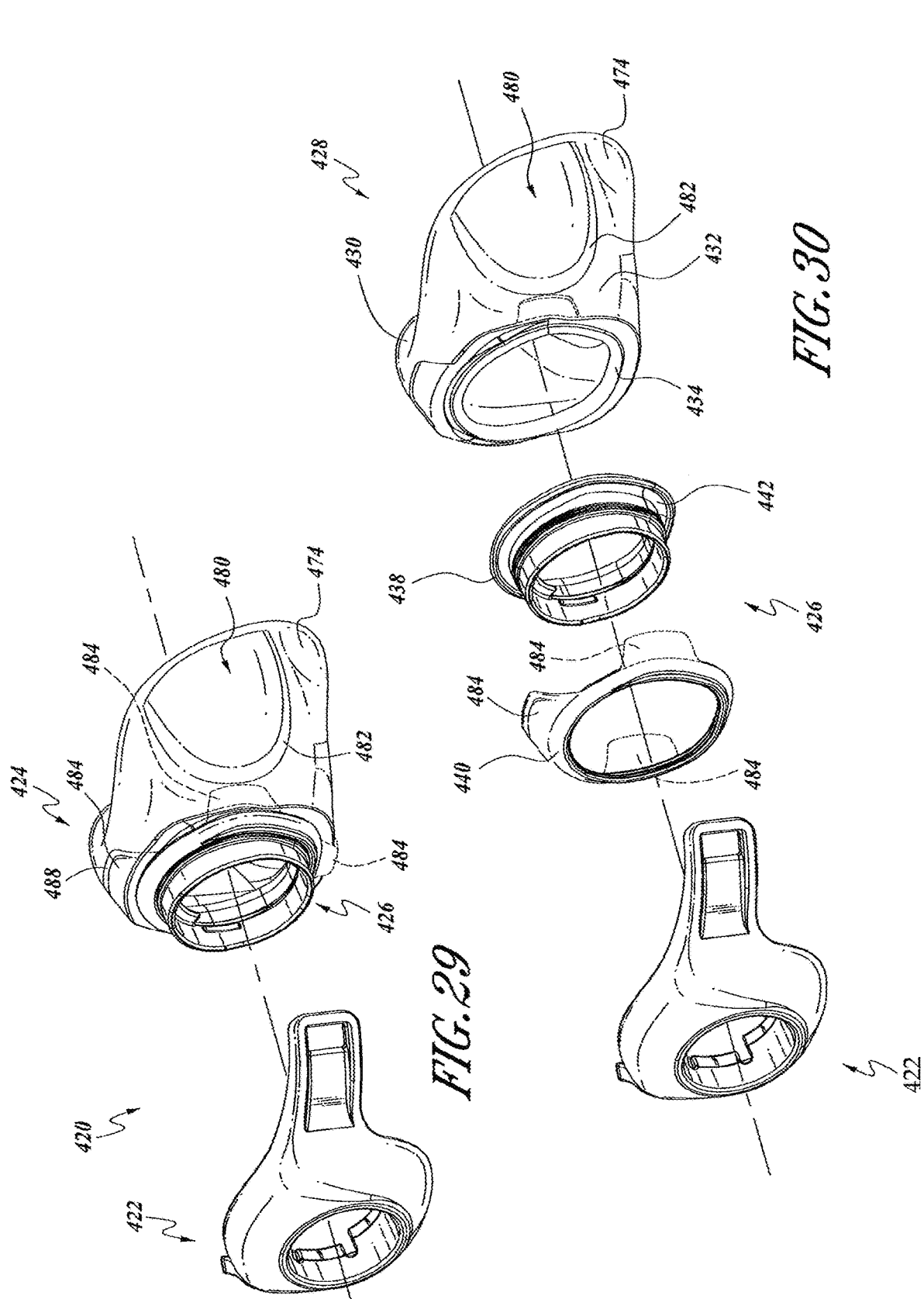
FIG. 29 is a partially exploded perspective view of an interface assembly that is arranged and configured in accordance with certain features, aspects and advantages of the present invention.
FIG. 30 is a more fully exploded perspective view of the interface assembly of FIG. 29.
Figure 31:
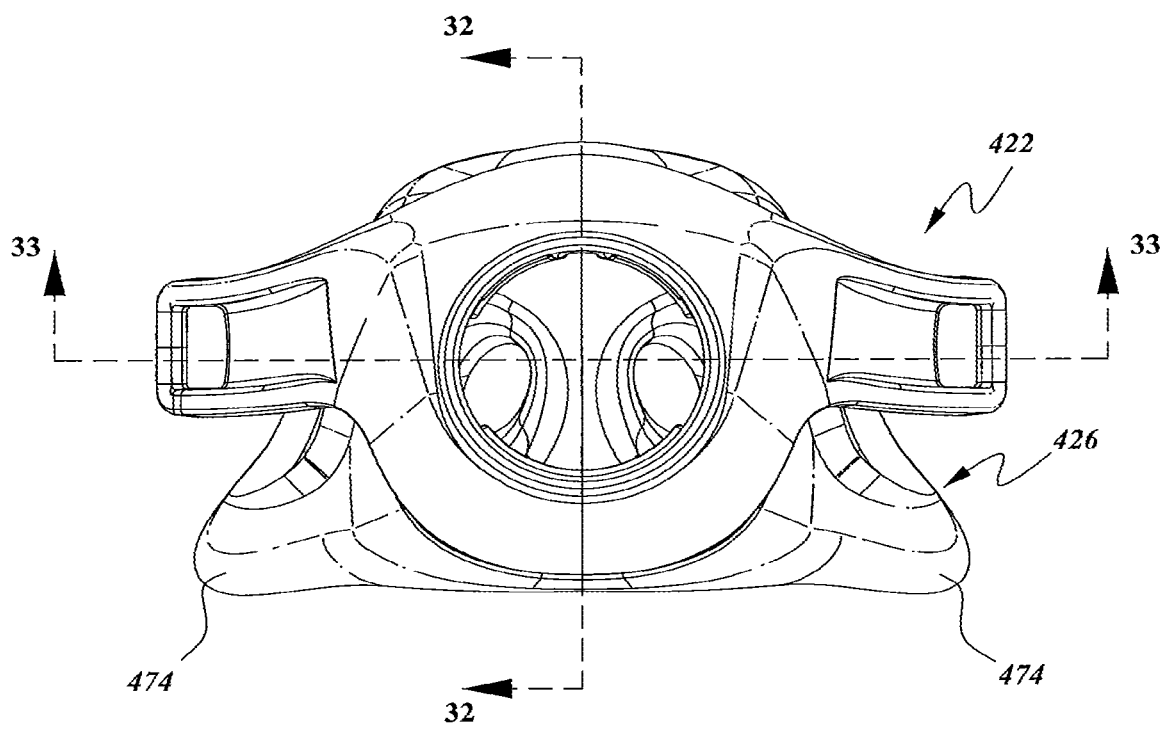
FIG. 31 is a perspective view of the interface assembly of FIG. 29.
Figure 32:
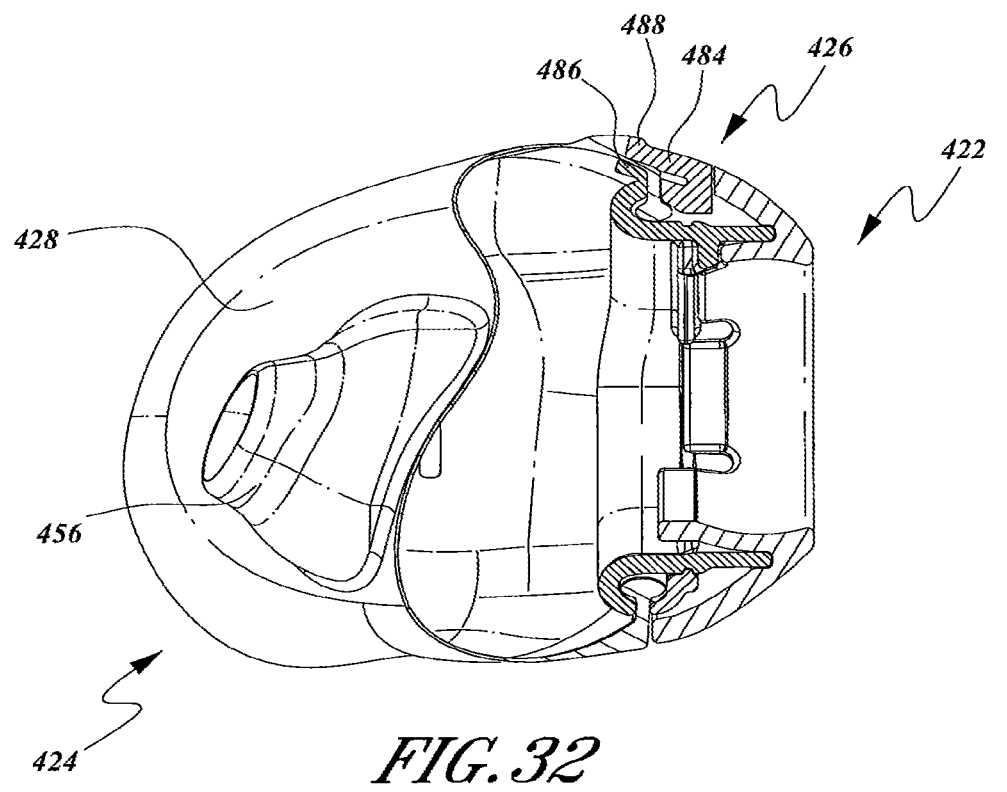
FIG. 32 is a sectioned view taken along the line 32-32 in FIG. 31.
Figure 33:
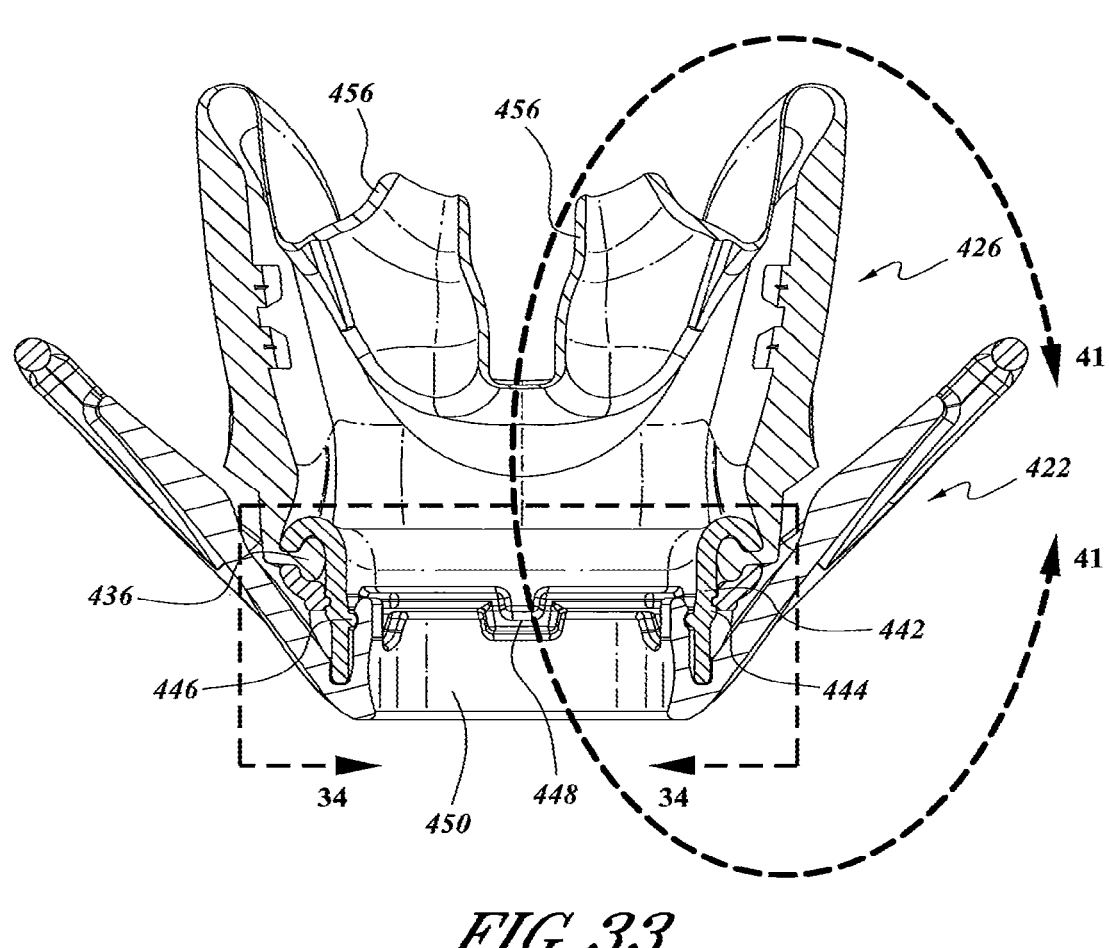
FIG. 33 is a sectioned view taken along the line 33-33 in FIG. 32.
Figure 34:
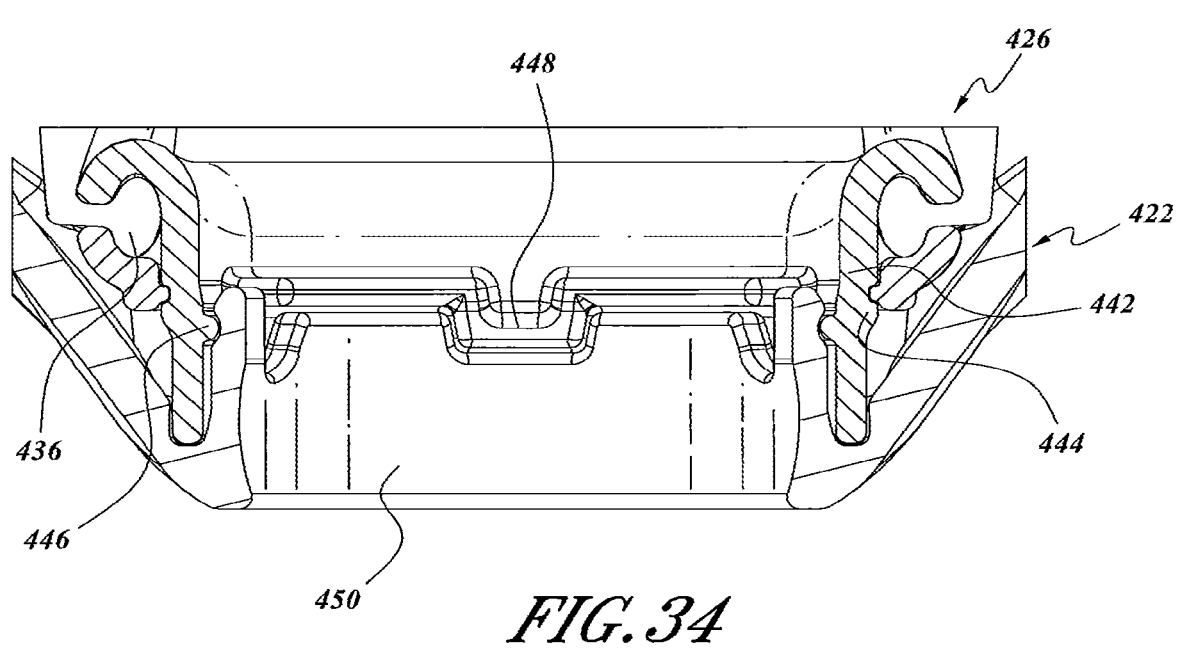
FIG. 34 is an enlarged view of a portion of FIG. 33.
Figures 35, 36, 37, 38, 39, 40:
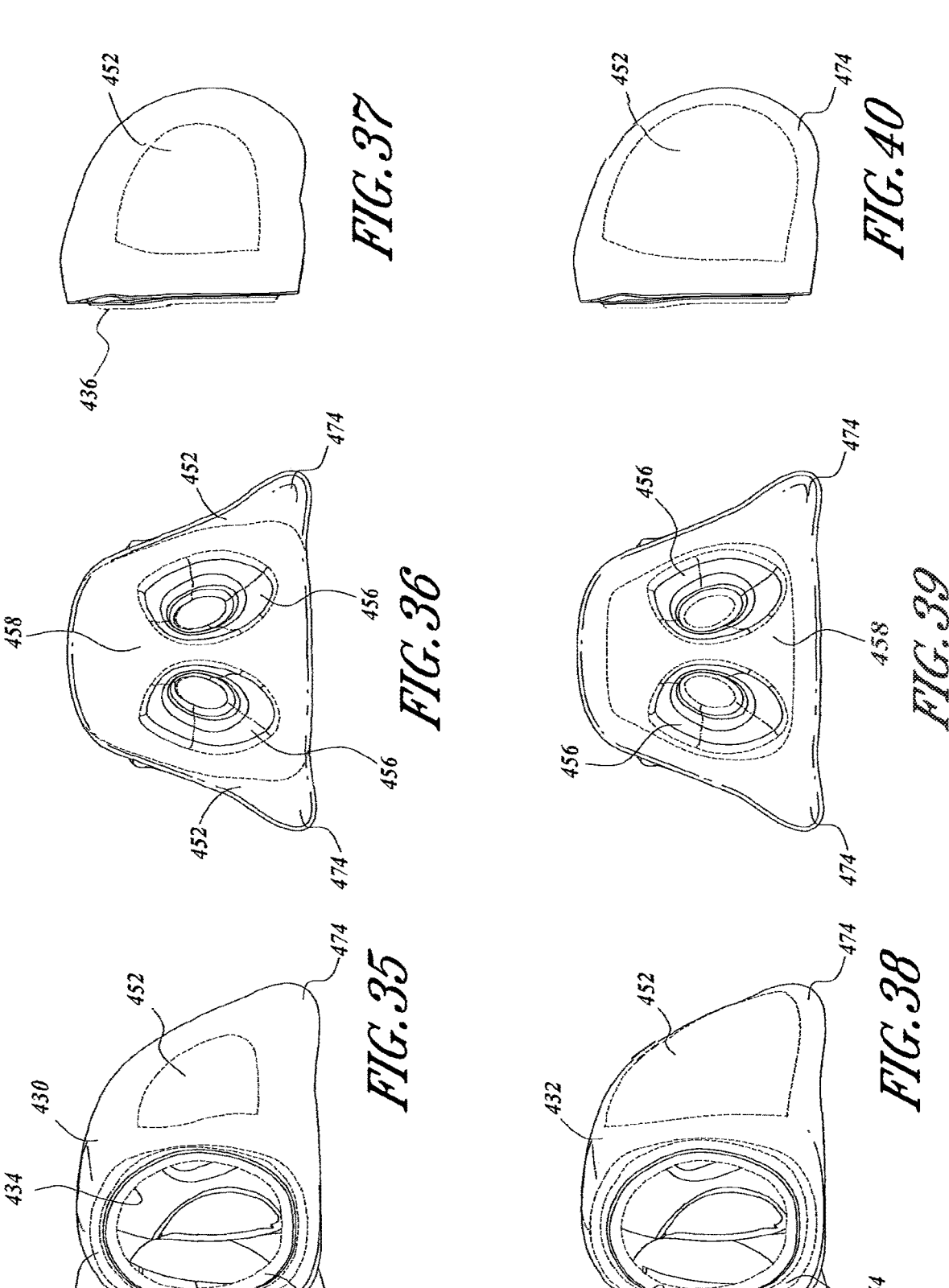
FIGS. 35-37 are views of a seal member of the interface assembly of FIG. 29 illustrating material thicknesses of the proximal wall.
FIGS. 38-40 are views of the seal member illustrating material thicknesses of the distal wall.

The illustrated seal 424 incorporates a connecting or mounting assembly 426 that can be joined to the flexible seal member 428. With reference to FIG. 30, the seal member 428 comprises a proximal surface 430 (i.e., the surface that is closest to the face of the user in use) and a distal surface 432 (i.e., the surface further away from the face of the user in use). In the illustrated configuration, the distal surface 432 defines an inlet opening 434. The opening 434 is configured to admit breathing gases into a chamber defined within the seal member 428.

In the illustrated configuration, the opening 434 is circumscribed by a rib or protrusion 436. The rib or protrusion 436 is best shown in the sectioned view of FIG. 34. As illustrated, a portion of the seal member 428 that connects the rib or protrusion 436 to the distal surface 432 can extend generally normal or perpendicular to an axis of the inlet opening 434. Thus, the rib or protrusion 436 is offset inwardly by a portion of the distal surface 432. The radial offset allows the rib or protrusion to be captured by the mounting assembly 426. Other configurations also are possible keeping in mind a desire to surface a more rigid mounting assembly 426 to the seal member 428.

The mounting assembly 426 can be more rigid than the seal member 428. In some configurations, the mounting assembly 426 can be formed as a two piece construction. For example, the mounting assembly 426 can capture the seal member 428 with an inner member 438 and an outer member 440. The inner member 438 can be inserted through the inlet opening 434.

The inner member can have a sleeve 442 that extends through the inlet opening 434. The sleeve 442 can join with a larger diameter ridge 444. The larger diameter ridge 444 can provide a location against which the rib or protrusion 436 of the seal member 428 can rest. The sleeve 442 can be externally threaded or include one or more outer protrusions 444. The sleeve 442 also can include an inner coupler construction 446. The outer threading or protrusions 444 can marry with a structure formed on an inner surface of the outer member 440. The outer member extends radially outward sufficiently to capture the rib or protrusion 436 of the seal member 428 between the outer member 440 and the inner member 438. In such a way, the mounting assembly 426 can be secured to the seal member 428.

As described above, the sleeve 442 of the inner member 438 includes the inner coupler construction 446. The inner coupler construction 446 mates with a corresponding structure on the frame 422 such that the seal 424 (i.e., seal member 428 and mounting assembly 426) can be secured to the frame 422 for use and removed for replacement. The frame 422 can have a flange or the like with which the mounting assembly 426 is connectable. In the illustrated configuration, an inlet portion of the frame 422 (i.e., a socket for a ball and socket connection) can incorporate a recess while the mounting assembly 426 can incorporate a ridge but other suitable constructions can be used keeping in mind a desire for a secure enough connection for use but a removable connection for replacement of the seal 424.

In some configurations, the frame 422 and the mounting assembly 426 can include orientation features. For example, in the illustrated configuration, the mounting assembly 426 can incorporate a tongue, protrusion or boss feature 448 while the frame 422 can incorporate a groove, recess or relief feature 450. With the tongue 448 aligned with the groove 450, the desired orientation between the seal 424 and the frame 422 can be ascertained. Other suitable configurations can be used keeping in mind a desire to obtain confirmation of correct alignment and orientation of the seal 424 to the frame 422.

With reference now to FIGS. 35-42, the seal member 428 of one preferred construction will be described in further detail. As has been described, the seal member 428 can have regions of increased suppleness and regions of increased stiffness. The regions can result from differing materials, differing grades of the same material or differing thicknesses. In the illustrated configuration, there are regions of differing thickness. The thickest regions on the proximal surface 430 (shown in FIGS. 35-37) and the thickest regions on the distal surface 432 (shown in FIGS. 38-40) can be found in the rib or protrusion 436 surrounding the inlet opening 434 and in a central portion of the wings 452. These regions are the regions used for mounting and for gripping and, as such, desirably are the thickest and stiffest regions. In addition, at least in the wing regions 452, the thickest regions can support the thinner regions and provide some structure to the seal member 428, as described below in greater detail. In some configurations, the thickness is 3.0 mm with some variation being possible slightly higher and lower keeping in mind a desire for this region to be sufficiently rigid for mounting and gripping.

The next thickest region is the joining region 454 that joins the rib or protrusion 436 to the balance of the seal member 428. This region simply is thick enough to resist tearing of the seal member 428 at the connection between the rib or protrusion 436 and the balance of the seal member 428. In some configurations, the joining region 454 has a thickness of about 1.0 mm with some variation being possible slightly higher and lower keeping in mind a desire to reduce or eliminate the likelihood of tearing during normal use.

As described above, nostril locators 456 can be positioned on the proximal surface 430. The nostril locators 456 desirably are sufficiently supple to reduce or eliminate the likelihood of causing irritation. The nostril locators 456 also desirably are sufficiently stiff to reduce the likelihood of ballooning or being insufficiently self-supporting to provide an indication to the user of correct location and orientation of the seal 424 relative to the face. Preferably, the nostril locators 456 have sufficient stiffness to inhibit or prevent significant collapse in response to positioning of the locators 456 in the user's nostrils. In some configurations, the nostril locators 456 can have a thickness of about 0.7 mm with some variation being possible slightly higher and lower keeping in mind a desire to reduce user discomfort while still assisting with mask positioning.

As described above, some regions of the seal member 428 can be configured for ballooning, inflating or the like. By having such distensible surfaces, the seal member 428 can provide more effective sealing while accommodating slight movements of portions of the seal member 428 relative to the face of the user in use. In effect, the nostril locators 456 can be somewhat decoupled from the frame 422 through the most supple regions of the seal member 428, which regions surround and isolate the nostril locators 456 from the balance of the mask in the illustrated configuration. As such, a surround region 458 can be defined to generally encircle the nostril locators 456. The surround region 458 can extend to a transition between the proximal surface 430 and the distal surface 432. In some configurations, the surround region 458 has a thickness of about 0.25 mm with some variation being possible slightly higher and lower keeping in mind a desire to allow some decoupling between the relatively more rigid nostril locators 456 and the balance of the seal member 428.

Other than the identified regions, the remainder of the illustrated seal member 428 can be a transition of wall thicknesses among the identified wall thicknesses. The illustrated seal member 428 is but one desired configuration and certain variations are possible.

As described above, as illustrated in FIG. 41 among others, the side portions or wing regions 452 can comprise stiffened regions in the form of thickened regions 470 that support thinner regions of the body of the seal member 428, such as the surround region 458. The thickened regions 470 can be mirror images of one another, as can the wing regions 452 such that the seal member 428 has symmetry about a central, vertical plane. The thickened regions 470 can extend along a substantial portion of the length and/or height of the wing regions 452 or of the seal member 428. In the illustrated arrangement, the thickened regions 470 extend substantially the entire length and substantially the entire height of the wing regions 452, which wing regions 452 can extend substantially the entire height and length of the seal member 428. Thus, in some configurations, the thickened regions 470 are essentially the same size and shape as the distal surfaces 432 of the wing regions 452.

The thickened regions 470 can be of substantially constant or varied thickness. In the illustrated arrangement, peripheral portions or edge portions of the thickened regions 470 are reduced in thickness relative to central portions of the thickened regions 470. In particular, forward edge portions of the thickened regions 470 reduce in thickness relative to adjacent portions and/or central portions and transition into the joining region 454 and rib 436 to accommodate the mounting assembly 426. Preferably, the forward edge portions of the thickened regions 470 have a greater thickness than the joining region 454 at least until a junction between the thickened regions 470 and the joining region 454. In the illustrated configuration, the forward edge portions of the thickened regions 470 gradually reduce in thickness toward the junction with the joining region 454.

Similarly, rearward edge portions of the thickened regions 470 also reduce in thickness relative to adjacent portions and/or central portions of the thickened regions 470. Such an arrangement preserves the suppleness of the rearward edge portions of the proximal surface 430 while inhibiting or preventing significant ballooning or distending of the rearward edge portions of the distal surface 432. Advantageously, such an arrangement allows the seal member 428 to provide adequate sealing functionality on outside portions of the user's nose while also providing a feeling of stability for the user because any significant ballooning of the rearward edge portions of the distal surface 432 can be limited or avoided.

Figure 41:
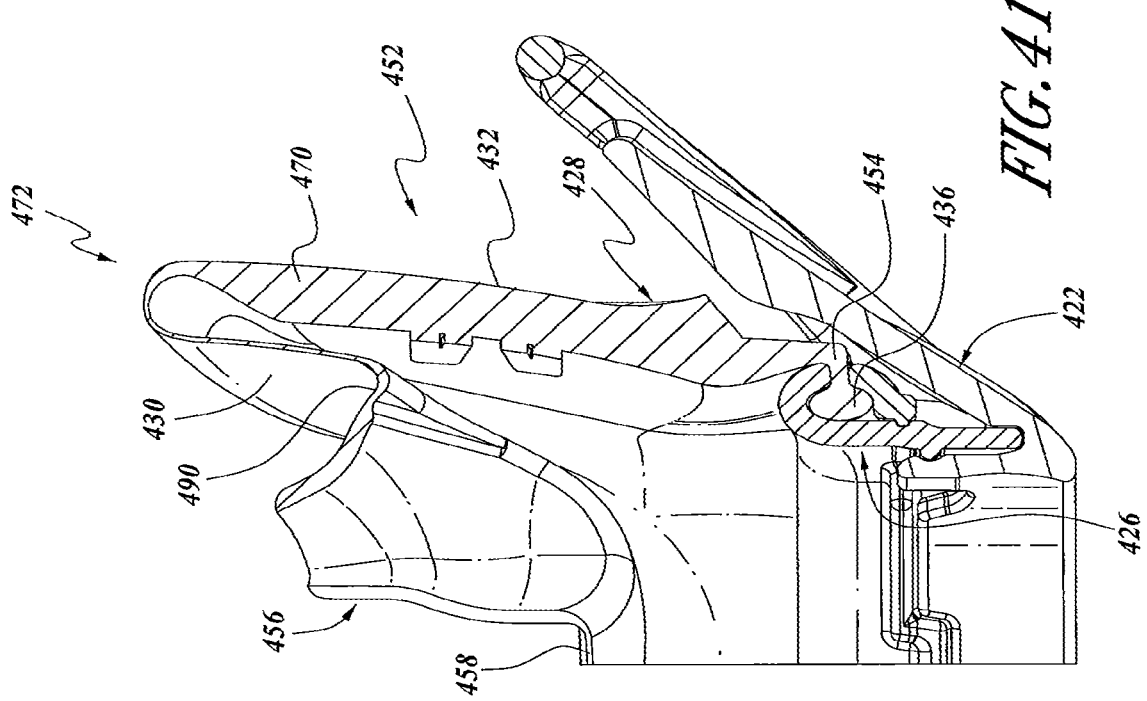
FIG. 41 is an enlarged view of a portion of the section of the seal member shown in FIG. 33.

With reference to FIG. 41, a rearward edge of the seal member 428, which can also be referred to as a rim or marginal surface, can comprise a transition portion 472 between the proximal surface 430 and the distal surface 432. In the illustrated configurations, the transition portion 472 comprises a generally rounded or curved wall portion. As described, in some configurations, the thickened regions 470 begin to taper in thickness forward of the transition portion 472. However, preferably, a portion of the transition portion 472 has a greater thickness than the supple proximal surface 430 or surround region 458 to control ballooning of the seal member 428 and, preferably, limit or prevent any substantial ballooning of the distal surface 432. In the illustrated arrangement, the rearward edge portions of the thickened regions 470 taper in thickness relatively quickly toward the transition portion 472, which then gradually tapers in thickness from the distal surface 432 to the proximal surface 430. In some configurations, the transition portion 472 can have a portion defining a wall thickness that is approximately the same as the thickness of the supple proximal surface 430, such as the surround region 458.

As illustrated in FIGS. 29-31, 35, 36 and 38-40, possibly among others, the lower, rearward corners of the wing regions 452 comprise outwardly-protruding portions or outwardly-protruding corners 474. The outwardly-protruding corners 474 flare outwardly relative to adjacent portions of the wing regions 452 to be positioned generally at locations corresponding to the check or upper lip of the user laterally outward of the nose. In some configurations, the outwardly-protruding corners 474 are located approximately over the portions of the upper lip overlying the canine or cuspid teeth of the user. The outwardly-protruding corners 474 can assist in anchoring the seal member 428 on the user's face. In some configurations, this arrangement allows additional stability elements to be omitted while still providing the user with a sense of sufficient stability such that the seal member 428 is the only portion of the mask that contacts the user's face. The sense of stability can be communicated to the user at least partially due to the outwardly-protruding corners 474 having a relatively high stiffness. Thus, preferably, the thickened regions 470 extend at least partially into to the outwardly-protruding corners 474 and, in some configurations, can extend at least substantially completely through the outwardly-protruding corners 474. Preferably, at least the rearmost and lowermost portions of the distal surface 432 of the seal 424 comprise the thickened regions 470. Within the outwardly-protruding corners 474, the thickened regions 470 can taper in thickness into the transition portion 472 as described above.

As described above, the wing regions 452 can be used as gripping portions of the seal 424 for the initial positioning of the mask on the face, repositioning of the mask on the face, removing or coupling the seal 424 from or to the frame or body 422, among other reasons. As described, the thickened regions 470 can facilitate gripping of the seal 424 on the distal surface within the wing regions 452 by limiting collapse of the seal 424 in response to squeezing of the wing regions 452. In some configurations, the distal surface 432 of the seal 424 can include surface features (e.g., one or more recesses or protrusions) configured to facilitate gripping. Such features can be referred to as grip surfaces or grips.

The illustrated wing regions 452 cach include a grip surface 480 formed by a protrusion 482. The protrusion 482 extends outwardly from adjacent surfaces to an extent sufficient to provide some degree of resistance to slipping of a user's fingers along the surface of the seal 424. The illustrated protrusion 482 is generally crescent-shaped, which defines a generally scallop-shaped grip surface 480. The ends of the protrusion 482 are positioned rearward of the center, curved portion of the protrusion 482. The user's fingers or thumb can be placed in the grip surface 480 and the user can push against the protrusion 482 when mounting the seal 424 to the frame or body 422. Thus, the protrusion 482 compensates for the inwardly-tapered or curved shape of the seal 424 that may otherwise allow the user's fingers or thumb to slide along the distal surface 432 of the seal 424. The grip surface 480 and/or protrusion 482 may also assist the user in removing the seal 424 from the frame or body 422 or otherwise positioning or repositioning the mask. Other suitable grip arrangements can also be provided, such as multiple protrusions, recesses or other surface features that enhance grip relative to a smooth surface. Materials or material treatments that improve grip could also be employed.

The seal 424 could alternatively or additionally include other features that define grip surfaces or grips. For example, with reference to FIGS. 29, 30 and 32, the seal 424 can include a relatively rigid grip 484. In the illustrated arrangement, the rigid grip 484 is defined by a rigid support member of the seal 424, such as the mounting assembly 426 and, in particular, the outer member 440 of the mounting assembly 426. The illustrated grip 484 is defined by a rearwardly-protruding portion or tab of the outer member 440, which can extend rearwardly of an annular portion of the outer member 440 over the distal surface 432 of the seal 424. The seal 424 can define a recess that accepts the grip 484 and an outer surface of the grip 484 can be aligned with an adjacent outer surface of the seal 424. The inner member 438 can include a portion 486 that also extends rearwardly in general alignment with the grip 484 but within the interior space of the seal 424 to capture the seal between the grip 484 and the rearward extending portion 486 of the inner member 438. The grip 484 can define one or more surface features 488 that enhance grip, such as one or more protrusions or recesses.

The illustrated grip 484 is located on the top of the seal 424. Additional or alternative locations include the bottom of the seal 424 or either side of the seal 424. For example, opposed pairs of grips 484 can be provided on the top and bottom and/or sides of the seal 424. In some configurations, the grip surfaces 480 and/or protrusion 482 can be defined by a rigid structure, such as a portion (e.g., the outer member 440) of the mounting assembly 426. In some configurations, the mounting assembly 426 can include protruding portions or other rigid portions can be provided that extend a substantial length and/or height of the wing regions 452 of the seal 424.

As described above, the nostril locators 456 can be at least somewhat decoupled from balance of the seal member 428. In some configurations, the seal member 428 can be configured to provide for or facilitate preferential movement of the nostril locators 456. In some such configurations, the seal member 428 can be configured to provide less resistance to tilting movement in at least one direction relative to at least one other direction. Preferably, the seal member 428 includes one or more features that provide for or facilitate outward tilting of the nostril locators 456 away from one another. That is, preferably, less resistance is provided for outward tilting of the nostril locators 456 relative to tilting in one or more other directions (e.g., inward, upward or downward). Such an arrangement can reduce discomfort that could otherwise occur as a result of the nostril locators 456 pinching the septum of the user's nose. The arrangements disclosed herein can be applied to other types of seals or patient interfaces, such as any arrangements incorporating nasal pillows or other sealing or non-scaling prong-like nasal elements.

Any suitable arrangement or structure can be used to provide for or facilitate preferential movement of the nostril locators 456. In the illustrated arrangement, the seal member 428 includes thinned regions extending around at least a portion of the nostril locators 456, which facilitate tilting or deflection of the nostril locators 456 and are referred to herein as deflection regions 490. In some configurations, the deflection regions 490 are located in annular transition portions surrounding the nostril locators 456 between the nostril locators 456 and the surround region 458. The transition portions can be formed partially or completely by the base portions of the nostril locators 456, partially or completely by the portions of the surround region 458 adjacent the base portions of the nostril locators 456 or a combination of the two. In other configurations, the deflection regions 490 can be provided in another suitable location to allow preferential deflection of the nostril locators 456.

In some configurations, the deflection regions 490 are located on the bases of the nostril locators 456 and, in the illustrated arrangement, substantially completely on the bases of the nostril locators 456. The deflection regions 490 can comprise thin-walled sections of the bases of the nostril locators 456. The thin-walled sections have a lower thickness than other portions of the nostril locators 456. In some configurations, the thin-walled sections defining the deflection regions 490 can be the thinnest portions of the nostril locators 456. In some configurations, the thin-walled sections have a wall thickness that is about one-half or less than about one-half of a wall thickness of a substantial portion or a remainder of the nostril locators 456. For example, in some configurations, the thin-walled sections of the deflection regions are about 0.35 mm thick and at least the primary portions of the nostril locators 456 are about 0.8 mm thick. In some configurations, the tips of the nostril locators 456 are thinned for comfort. However, with the provision of the deflection regions 490, the tips can be the same or substantially the same wall thickness as other portions of the nostril locators 456 to improve user feedback and inhibit collapse upon insertion into the nostrils while also being comfortable during use. The thin-walled sections defining the deflection regions 490 can have a greater thickness than the surround region 458.

The deflection regions 490 preferably extend around only a portion of the respective perimeters of the nostril locators 456. In some configurations, the deflection regions 490 are limited to about one-half or less of the perimeters of the nostril locators 456.

In some configurations, the deflection regions 490 are limited to an outer side of the perimeters of the nostril locators 456. In the illustrated arrangement, the deflection regions 490 extend around greater than or equal to about one-third, but less than or equal to about one-half of the respective perimeters of the nostril locators 456.

Figure 42:
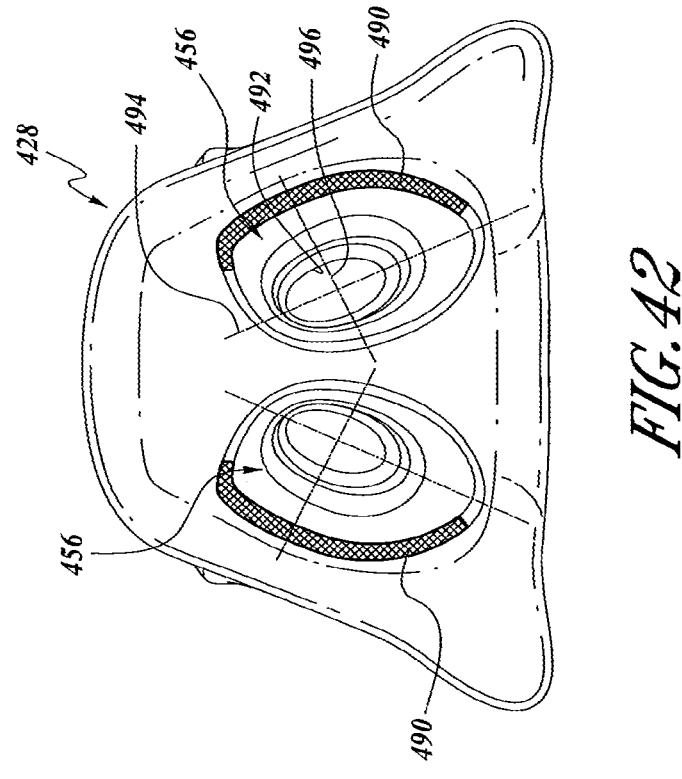
FIG. 42 is a rear view of the seal member of the interface assembly of FIG. 29.

With reference to FIG. 42 in particular, the outlet apertures 492 defined by the nostril locators 456 are generally oval in shape and each define a major axis 494 along the largest width of the outlet aperture 492 and a minor axis 496 that is perpendicular to the major axis 494. In some configurations, the deflection region 490 is substantially or completely limited to one side (e.g., the outer side) of the major axis 494. A lower end of the deflection region 490 can be at or near the major axis 494 and an upper end of the deflection region 490 can be spaced from the major axis 494. Such an arrangement can permit tilting in an outward and slightly downward direction relative to the major axis 494. The length and/or position of the deflection regions 490 can be altered to provide for a desired direction of tilting or deflection. In some configurations, if the lower end of the major axis 494 is assumed to be 0 degrees, the deflection regions 490 can extend from about 5 degrees to about 150 degrees.

At least in part because of the provision of the deflection regions 490 and other features described herein, the geometry of the seal member 428 of FIGS. 29-42 has been modified relative to the geometry of the nasal seal presently commercialized by the Applicant, Fisher & Paykel Healthcare Limited, in the Pilairo® nasal mask. For example, the major axes 494 have been rotated toward vertical by about 10 degrees relative to the orientations of the current Pilairo® nasal mask. Relative to a central, vertical plane passing through the seal member 428, the major axes 494 are oriented at an angle of about 20-25 degrees with the lower ends of the major axes 494 being further outward (further from the central plane) than the upper ends of the major axes 494. The surface defining the tips of the nostril locators 456 have been rotated outwardly by about 4 degrees relative to the current Pilairo® nasal mask such that the surfaces define an angle of about 20-25 degrees with the central plane with the outer portions of the tips of the nostril locators 456 being further rearward than the inner portions. The length of the nostril locators 456 has been reduced by about 1 mm to about 11 mm. The outlet aperture 492 defines a more round shape. For example, the dimension along the major axis 494 can be about 10 mm and the dimension along the minor axis can be about 5.5 mm. The nostril locators 456 are also spaced slightly wider apart. For example, the spacing of the major axes 494 at the bases and the tips of the nostril locators 456 can be about 18.5 mm and about 11 mm, respectively.

Figure 43:
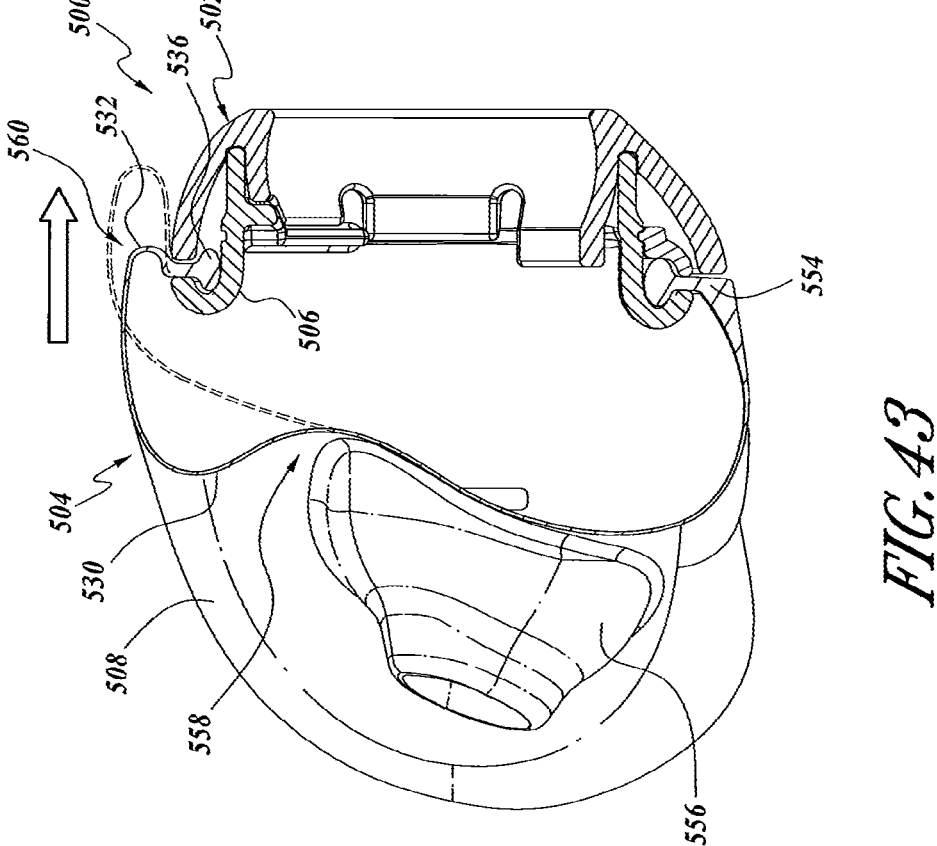
FIG. 43 is a sectioned view of another interface assembly that is arranged and configured in accordance with certain features, aspects and advantages of the present invention.

With reference to FIG. 43, a further interface assembly 500 is illustrated that is arranged and configured in accordance with certain features, aspects and advantages of the present invention. The interface assembly 500 generally comprises a frame or body 502 and a seal 504. The seal 504 can be removably secured to the frame 502 for use. In the illustrated configuration, the frame 502 provides attachment points for headgear or the like. The illustrated seal 504 incorporates a connecting or mounting assembly 506 that can be joined to the flexible seal member 508. The seal member 508 comprises a proximal surface 530 (i.e., the surface that is closest to the face of the user in use) and a distal surface 532 (i.e., the surface further away from the face of the user in use). The interface assembly 500 is described in the context of the differences relative to other interface assemblies described herein. Thus, features that are not described can be assumed to be the same as or similar to corresponding features of the other interface assemblies disclosed herein, or can be of another suitable arrangement.

The seal member 508 of FIG. 43 preferably includes features that facilitate or promote deflection of an upper, central portion of the seal member 508 that is aligned with the user's nose to inhibit or prevent excess pressure from being applied to the nose. In some configurations, portions of the seal member 508 defining both the proximal surface 530 and the distal surface 532 in the central portion deflect forwardly to accommodate a user's nose. That is, in some configurations, the entire upper, central portion of the seal member 508 can deflect in a forward direction rather than the proximal surface 530 simply moving closer to the, often substantially stationary, distal surface 532, which can cause stretching of the proximal surface 530 and, thus, discomfort. Deflection of the seal member 508 may not occur in all situations. For example, certain facial geometries may result in little to no deflection, while other facial geometries may result in significant deflection.

The illustrated seal member 508 includes a rib or protrusion 536 that provides for connection to the connecting or mounting assembly 506. A joining region 554 can connect the rib or protrusion 536 to the balance of the seal member 508. In some configurations, portions of the joining region 554 can have a thickness of about 1.0 mm with some variation being possible slightly higher and lower keeping in mind a desire to reduce or eliminate the likelihood of tearing during normal use. However, the upper, central portion 560 of the seal member 508, which may include portions of the joining region 554, preferably has a lower wall thickness to facilitate or promote deflection (illustrated in broken line). The wall thickness of the upper, central portion 560 can be the same as or similar to the surround region 458 of the seal member 428 of FIGS. 29-42, such as about 0.25 mm, for example. In some configurations, the upper, central portion 560 can be connected to or integrated with a surround region 558, which surrounds nostril locators 556 of the seal member 508. In the illustrated arrangement, the reduced wall thickness of the upper, central portion 560 begins substantially immediately outward of the connecting or mounting assembly 506. Other suitable arrangements to permit deflection and/or rolling movement of the upper, central portion 560 of the seal member 508 can also be used, such as the concepts and arrangements disclosed in WO 2014/062070, the entirety of which is incorporated by reference herein.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. A nasal seal configured to be removably coupled to a frame of a patient interface, the nasal seal comprising:
    a seal body formed of a soft flexible material and defining an inner cavity and one or more delivery openings for supply of breathing gases from the inner cavity to a patient;
    wherein the seal body comprises a central portion and a side portion extending from each end of the central portion, the seal body further comprising an interior side and an exterior side, wherein a central interior portion of the interior side within the central portion is configured to extend across a base of a user's nose and a side interior portion of the interior side within each of the side portions is configured to extend across a side of the user's nose, wherein the interior side of the seal body is supple and configured to conform under internal pressure to surfaces of the user's nose, including, at the side interior portions of the seal body, to outside surfaces of sides of the user's nose, wherein each of the side portions defines a transition portion between the exterior side and the interior side, wherein the exterior side of each of the side portions comprises stiffened regions that are stiffer or much stiffer than the supple interior side, the stiffened regions extending to or substantially to the transition portions, wherein rearmost and lowermost sections of the side portions flare outwardly relative to adjacent portions of the seal body, and wherein the stiffened regions extend at least partially into the outwardly flared rearmost and lowermost sections of the side portions.

2. The nasal seal of claim 1, wherein the stiffened regions extend at least substantially completely through the outwardly flared rearmost and lowermost sections of the side portions.

3. The nasal seal of claim 1, wherein the stiffened regions are formed by relatively thickened portions of the seal body.

4. The nasal seal of claim 3, wherein the relatively thickened portions taper in thickness before the transition portions.

5. The nasal seal of claim 1, wherein the transition portions include a portion that is thicker than the supple interior side.

6. The nasal seal of claim 1, wherein the stiffened regions extend substantially along an entire length of the exterior side of the seal body.

7. The nasal seal of claim 1, wherein the transition portions comprise rounded wall sections.

8. The nasal seal of claim 1, further comprising a support formed of a relatively rigid material that supports the seal body.

9. The nasal seal of claim 8, wherein the support defines at least one grip surface portion extending along the exterior side of the seal body.

10. The nasal seal of claim 9, wherein the at least one grip surface portion comprises at least one pair of grip surface portions substantially opposite one another.

11. The nasal seal of claim 8, wherein the support defines a mount for mounting the nasal seal to the frame.

12. The nasal seal of claim 11, wherein the mount comprises a first member that is connectable to a second member, wherein the first member and the second member capture a portion of the seal body between them.

13. The nasal seal of claim 12, wherein the first member is positioned within the inner cavity of the seal body and comprises a sleeve portion that extends outwardly from the inner cavity.

14. The nasal seal of claim 13, wherein the second member surrounds the sleeve portion of the first member.

15. The nasal seal of claim 1, wherein the central portion of the seal body defines a thinned region that permits forward movement of an upper portion of the interior side of the central portion as a result of rolling movement of the seal body.

16. The nasal seal of claim 1, wherein the one or more delivery openings comprises a first delivery opening and a second delivery opening, further comprising a nostril locator associated with and forming a portion of each delivery opening, wherein a deflection region is defined within an annular transition portion between each of the nostril locators and a surrounding portion of the interior side, wherein the deflection region has a lower stiffness relative to another region of the annular transition portion not within the deflection region.

17. The nasal seal of claim 16, wherein the lower stiffness is achieved by the deflection regions having a smaller thickness than the other regions of the annular transition portion.

18. The nasal seal of claim 16, wherein the deflection regions are located on outer sides of the nostril locators.

19. The nasal seal of claim 18, wherein the deflection regions provide less resistance to outward tilting of the nostril locators relative to tilting in one or more other directions.

20. The nasal seal of claim 16, wherein the deflection regions are limited to less than or equal to one-half of the annular transition portion.

21. The nasal seal of claim 16, wherein the deflection regions are greater than or equal to one-third of the annular transition portion.

22. The nasal seal of claim 16, wherein the outwardly flared rearmost and lowermost sections of the side portions form outwardly protruding corners of the seal body.

\* \* \* \* \*